(12) United States Patent
Nunokawa et al.

(10) Patent No.: US 6,734,180 B1
(45) Date of Patent: *May 11, 2004

(54) NF-κB INHIBITOR COMPRISING AN INDAN DERIVATIVE AS AN ACTIVE INGREDIENT

(75) Inventors: Yoichi Nunokawa, Toyonaka (JP); Takashi Nakatsuka, Osaka (JP); Masayuki Saitoh, Ibaraki (JP); Keiichi Abe, Ikeda (JP)

(73) Assignee: Daiichi Suntory Pharma Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 194 days.

(21) Appl. No.: 09/532,935

(22) Filed: Mar. 22, 2000

Related U.S. Application Data

(63) Continuation of application No. PCT/JP99/03938, filed on Jul. 22, 1999, now abandoned.

(30) Foreign Application Priority Data

Jul. 22, 1998 (JP) .......................................... 10-206929

(51) Int. Cl.$^7$ .................... C07D 473/34; C07D 487/04; C07D 491/048; A61K 31/505; A61K 31/52
(52) U.S. Cl. .................... 514/234.2; 544/280; 544/277; 544/255; 544/254; 544/279; 544/117; 514/258; 514/261
(58) Field of Search .................. 544/280, 277, 544/255, 254, 279, 117; 514/261, 258, 234.2

(56) References Cited

U.S. PATENT DOCUMENTS

| | | | |
|---|---|---|---|
| 3,470,182 A | 9/1969 | Hardtmann et al. | 260/256.4 |
| 4,501,735 A | 2/1985 | Trivedi et al. | 514/46 |
| 4,704,381 A | 11/1987 | Schaumann et al. | 514/46 |
| 4,985,409 A | 1/1991 | Yamada et al. | 514/46 |
| 5,541,343 A | 7/1996 | Himmelsbach et al. | 514/424 |

FOREIGN PATENT DOCUMENTS

| | | |
|---|---|---|
| EP | 0253321 A2 | 1/1988 |
| JP | 55-100346 | 7/1980 |
| JP | 60-193998 | 10/1985 |
| JP | 63-23853 | 2/1988 |
| JP | 2-184649 | 7/1990 |
| JP | 5-310743 | 11/1993 |
| JP | 5-310748 | 11/1993 |
| JP | 9-227561 | 9/1997 |
| JP | 10-87491 | 4/1998 |
| JP | 10-87492 | 4/1998 |
| WO | 96/35430 | 11/1996 |
| WO | 97/09315 A1 | 3/1997 |
| WO | 97/09315 | 3/1997 |
| WO | 97/09325 A1 | 3/1997 |
| WO | 97/09325 | 3/1997 |

OTHER PUBLICATIONS

Shinichi, Xanthine Derivative, Patent Abstracts of Japan, Publication No. 09227561, Sep. 2, 1997.
Yasuri, Transcription Control Factor Inhibitor, Patent Abstracts of Japan, Publication No. 10087491, Apr. 7, 1988.
Salvador Moncada, M.D. et al, "The L–Arginine–Nitric Oxide Pathway," The New England Journal of Medicine, vol. 329, No. 27, pp. 2002–2012, 1993.
Ulrich Forstermann et al, "Properties, Cellular Distribution and Expressional Control," Biochemistry Pharmacology, vol. 50, No. 9, pp. 1321–1332, 1995.
V. Cattell et al, "Inducible Nitric Oxide Synthase in Inflammation," Histochemical Journal, vol. 27, pp. 777–784, 1995.
Andreas K. Nussler et al, "Inflammation, Immunoregulation, and Inducible Nitric Oxide Synthase," Journal of Leukocyte Biology, vol. 54, pp. 171–178, 1993.
S. Moncada et al, "Molecular Mechanisms and Therapeutic Strategies Related to Nitric Oxide," The FASEB Journal, vol. 9, pp. 1319–1330, 1995.
Xiao–qing Wei et al, "Altered Immune Responses in Mice Lacking Inducible Nitric Oxide Synthase," Nature, vol. 375, pp. 408–411, 1995.
Jill E. Ogden et al, "Inhibition of Nitric Oxide Synthase –Potential for a Novel Class of Therapeutic Agent," Tibech, vol. 13, pp. 70–78, 1995.
R. Davis Manning, Jr. et al, "Cardiovascular Responses to Long–term Blockade of Nitric Oxide Synthesis," Hypertension, vol. 22, No. 1, pp. 40–48, 1993.
Garry J. Southan et al, "Selective Pharmacological Inhibition of Distinct Nitric Oxide Synthase Isoforms," Biochemical Pharmacology, vol. 51, pp. 383–394, 1996.
Pierre Vassalli, "The Pathophysiology of Tumor Necrosis Factors," Annu. Rev. Immunol., vol. 10, pp. 411–452, 1992.

(List continued on next page.)

Primary Examiner—Richard L. Raymond
Assistant Examiner—Hong Liu
(74) Attorney, Agent, or Firm—Burns, Doane, Swecker & Mathis, L.L.P.

(57) ABSTRACT

An inhibitor of NF-κB comprising as an active ingredient an indan derivative represented by the general formula (I) or a salt thereof.

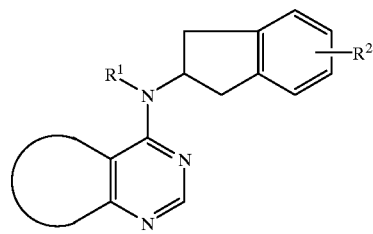

(I)

9 Claims, 1 Drawing Sheet

OTHER PUBLICATIONS

Yasutoshi Muto et al, "Enhanced Tumour Necrosis Factor and Interleukin–1 in Fulminant Heptatic Failure," The Lancet, pp. 72–74, 1988.

Mohammad K. Sharief, M.B. et al, "Association Between Tumor Necrosis Factor–α and Disease Progression in Patients with Multiple Sclerosis," The New England Journal of Medicine, vol. 325, No. 7, pp. 467–472, 1991.

Ciro Tetta et al, Tumour Necrosis Factor in Serum and Synovial Fluid of Patients with Active and Severe Rheumatoid Arthritis, Annals of the Rheumatic Diseases, vol. 49, pp. 665–667, 1990.

G. Venn et al, "Elevated Synovial Fluid Levels of Interleukin–6 and Tumor Necrosis Factor Associated with Early Experimental Canine Osteoarthritis," Arthritis and Rheumatism, vol. 36, No. 6, pp. 819–826, 1993.

Michael J. Elliott et al, "Repeated Therapy with Monoclonal Antibody to Tumour Necrosis Factor α (cA2) in Patients with Rheumatoid Arthritis," The Lancet, vol. 344, pp. 1125–1127, 1994.

Michael J. Elliot et al, "Randomised Double–Blind Comparison of Chimeric Monoclonal Antibody to Tumour Necrosis Factor α (cA2) Versus Placebo in Rheumatoid Arthritis," The Lancet, vol. 344, pp. 1105–1110, 1994.

E. C. C. Rankin et al, "The Therapeutic Effects of an Engineered Human Anti–Tumour Necrosis Factor Alpha Antibody (CDP571) in Rheumatoid Arthritis," British Journal of Rheumatology, vol. 34, pp. 334–342, 1995.

Jean–Louis Vincent, M.D., Ph.D. et al, "Administration of Anti–TNF Antibody Improves left Ventricular Function in Septic Shock Patients," Chest, vol. 101, No. 3, pp. 810–815, 1992.

L.B. Hinshaw et al, "Survival of Primates in $LD_{100}$ Septic Shock Following Therapy with Antibody to Tumor Necrosis Factor (TNFα)," Circulatory Shock, vol. 30, pp. 279–292, 1990.

U. Nyman et al, "Amelioration of Collagen II–Induced Arthritis in Rats by the Type IV Phosphodiesterase Inhibitor Rolipram," Clin Exp. Immunol., vol. 108, pp. 415–419, 1997.

Timothy S. Blackwell et al, "The Role of Nuclear Factor–kB in Cytokine Gene Regulation," Am. J. Respir. Cell Mol. Biol., vol. 17, pp. 3–9, 1997.

C. Victor Jongeneel, "Regulation of the TNFα Gene," Bacterial Endotoxins: Basic Science to Anti–Sepsis Strategies, pp. 367–381, 1994.

Qiao–wen Xie et al, "Role of Transcription Factor NF–kB/Rel in Induction of Nitric Oxide Synthase," The Journal of Biological Chemistry, vol. 269, No. 7, pp. 4705–4708, 1994.

Youichi Nunokawa et al, "Human Inducible Nitric Oxide Synthase Gene is Transcriptionally Regulated by Nuclear Factor–kB Dependent Mechanism," Biochemical and Biophysical Research Communications, vol. 223, pp. 347–352, 1996.

Tucker Collins et al, "Transcriptional Regulation of Endothelial Cell Adhesion Molecules: NF–kB and Cytokine–Inducible Enhancers," The FASEB Journal, vol. 9, pp. 899–909, 1995.

Patrick A. Baeuerle et al, "NF–kB as a Frequent Target for Immunosuppressive and Anti–Inflammatory Molecules," Advances in Immunology, vol. 65, pp. 111–137.

Bruce J. Dezube et al, "Cytokine Dysregulation in AIDS: In Vivo Overexpression of mRNA of Tumor Necrosis Factor–α and Its Correlation with That of the Inflammatory Cytokine GRO," Journal of Acquired Immune Deficiency Syndromes, vol. 5, No. 11, pp. 1099–1104, 1992.

Gary Nabel et al, "An Inducible Transcription Factor Activates Expression of Human Immunodeficiency Virus in T Cells," Nature, vol. 326, pp. 711–713, 1987.

Fatemeh Fazely et al, "Pentoxifylline (Trental) Decreases the Replication of the Human Immunodeficiency Virus Type 1 in Human Peripheral Blood Mononuclear Cells and in Cultured T Cells," Blood, vol. 77, No. 8, pp. 1653–1656, 1991.

Eduardo Munoz et al, "Activation of NF–kB by the Tax Protein of HTLV–1," Immunobiol, vol. 193, pp. 128–136, 1995.

Nathalie Auphan et al, "Immunosuppression by Glucocorticoids: Inhibition of NF–kB Activity Through Induction of IkB Synthesis," Science, vol. 270, pp. 286–290, 1995.

Rodney E. Shackelford et al, "Aspirin Inhibits Tumor Necrosis Factor–α Gene Expression in Murine Tissue Macrophages," Molecular Pharmacology, vol. 52, pp. 421–429, 1997.

Vira Bitko et al, "Transcriptional Induction of Multiple Cytokines by Human Respiratory Syncytial Virus Requires Activation of NF–kB and is Inhibited by Sodium Salicylate and Aspirin," Virology, vol. 232, pp. 369–379, 1997.

Robert W. Sullivan et al, "2–Chloro–4–(trifluoromethyl)pyrimidine–5–N–(3',5'–bis(trifluoromethyl)phenyl)–carboxamide: A Potent Inhibitor of NF–kB–and AP–1–Mediated Gene Expression Identified Using Solution–Phase Combinatorial Chemistry," J. Med. Chem., vol. 41, pp. 413–419, 1998.

B. K. Trivedi et al, "$N^6$–Substituted Adenosine Receptor Agonists: Potential Antihypertensive Agents," J. Med. Chem., vol. 34, pp. 1043–1049, 1991, pp. 6073–6077.

Aaron Bendich et al, "The Synthesis and Properties of 6–Chloropurine and Purine," Jul. 2, 1954.

Roland K. Robins, "Potential Purine Antagonist. I. Synthesis of Some 4,6–Substituted Pyrazolo [3,4–d]pyrimidines," 1955, vol. 78, pp. 784–790.

James P. Ferris et al, "Studies in Prebiotic Synthesis. I. Aminomalononitrile and 4–Amino 5–cyanoimidazole," Journal of the American Chemical Society, vol. 88, No. 6, 1966, pp. 3829–3831.

Edward C. Taylor et al, "Studies in Purine Chemistry. X. Some Derivatives of 9–Aminopurines," Apr. 17, 1961, pp. 4961–4967.

Edward C. Taylor et al, "The Synthesis of 4–Aminoisoxazolo[5,4–d]pyrimidines," Dec. 5, pp. 2116–2120, 1963.

Eiji Suzuki et al., "Studies on Pyrimidine Derivatives. X," Chem. Pharm. Bull., vol. 16, No. 4, pp. 750–755, 1967.

D.J. Brown et al, "Isomerisations Akin to the Dimroth Rearrangement. Part II. The Equilibria of 4–Mercapto–1,2,3,5,7–penta–azaindenes † with 4–Amino–1–thia–2,3,5,7–tera–azaindenes," J. Chem. Soc. (C), pp. 1856–1860, 1967.

K. Hartke et al, "A New Synthesis of Isothiazoles", Angew. Chem. internat. Edit., vol. 6, pp. 83–84, 1967.

K. Hartke et al, "3–Amino–4–isothiazolcarbonitrile und Isothiazolo[3,4–d]pyrimidine," pp. 611–621, Jan. 1968.

Horace A. DeWald et al, "Synthesis and Potential Antipsychotic Activity of 1H–Imidazo[1,2–c]pyrazolo[3,4–e]pyrimidines," J. Med. Chem. 1988, vol. 31, pp. 454–461.

Shirish A. Patil et al, "Synthesis of Some New Thieno[3,4–d]pyrimidines and their C–Nucleosides [1]," Med. Chem. Lab., vol. 30, pp. 509–515, 1993.

István Hermecz et al, "Nitrogen Bridgehead Compounds. 18.[1] New Antiallergic 4H–Pyrido[1,2–a]pyrimidin–4–ones. 1," J. Med. Chem., vol. 25, pp. 1140–1145, 1982.

David E. Nichols et al, "Nonneurotoxic Tetralin and Indan Analogues of 3,4–(Methylenedioxy)amphetamine (MDA)," J. Med. Chem., vol. 33, pp. 703–710, 1990.

Alicia Torrado et al, "General Synthesis of Retinoids and Arotinoids via Palladium–Catalyzed Cross–Coupling of Boronic Acids with Electrophiles," Synthesis, pp. 285–293, Mar. 1995.

Norio Miyaura et al, "Palladium–Catalyzed Cross–Coupling Reactions of Organoboron Compounds," Chem. Rev., vol. 95, pp. 2457–2483, 1995.

Takayuki Oh–e et al, "Palladium–Catalyzed Cross–Coupling Reaction of Organoboron Compounds with Organic Triflates," J. Org. Chem., vol. 58, pp. 2201–2208, 1993.

Gianfranco Cainelli, et al, "Clevage of Olefins by Polymer–Supported Osmium Tetroxide and Sodium Periodate," Communications, pp. 47–48, Jan. 1989.

E.J. Corey, et al, "New Methods for the Oxidation of Aldehydes to Carboxylic Acids and Esters", Journal of the American Chemical Society, vol. 90, No. 20, pp. 5616–5617, Sep. 25, 1968.

K.C. Nicolaou et al, "Total Synthesis of Epothilones A and B via a Macrolactonization–Based Strategy," J. Am. Chem. Soc., vol. 119, pp. 7974–7991, 1997.

Mario C. Filion et al, "Anti–inflammatory activity of cationic lipids", British Journal of Pharmacology, vol. 122, pp. 551–557, 1997.

Peter W. Tsao et al, "Rapid Communication The Effect of Dexamethasone on the Expression of Activated NF–kB in Adjuvant Arthritis," Clinical Immunology and Immunopathology, vol. 83, No. 2, May, pp. 173–178, 1997.

Salvatore Cuzzocrea et al, "Antiinflammatory Effects of Mercaptoethylguanidine, A Combined Inhibitor of Nitric Oxide Synthase and Peroxynitrite Scavenger, In Carrageenan–Induced Models of Inflammation," Free Radical Biology & Medicine, vol. 24, No. 3, pp. 450–459, 1998.

Yoshiki Sawa et al, "A Novel Strategy for Myocardial Protection Using In Vivo Transfection of cis Element 'Decoy' Against NFkB Binding Site –Evidence for a Role of NFkB in Ischemia–Reperfusion Injury," Gene Therapy for Myocardial Protection, pp. II–280–II285.

Herbert O. House et al, "Perhydroindan Derivatives. XII.[1] 6–Methoxyindanone and Its Derivatives," Dept. of Chem., Mass. Institute of Tech., Cambridge, Mass., vol. 35, No. 3, pp. 647–651, 1970.

Shoetsu Konno et al, "Synthesis of Thieno[2,3–d]pyrimidine Derivatives and Their Antifungal Activities," Pharmaceutical Institute, Tohoku Univ., vol. 109, pp. 464–473, 1989.

J. Davoll, "Pyrrolo[2,3–d]pyrimidines," J. Chem. Soc., pp. 131–138, 1960.

R. A. West et al, "1–Alkyl(aryl)–2,7–Dimethyl– 4–substituted Aminopyrrolo[2,3–d]pyrimidines," Contribution from the Wellcome Research Labs., pp. 3809–3812, 1961.

Aaron Bendich, et al, "The Synthesis and Properties of 6–Chloropurine and Purine," Contribution from the Labs. of the Sloan–Ketterine Division of Cornell Univ. Med. Coll., pp. 6073–6077, 1954.

James P. Ferris et al, "Studies in Prebiotic Synthesis. I. Aminomalononitrile and 4–Amino–5–cyanoimidazole[1,2]", Contribution from the Salk Institute for Biological Studies, LaJolla, California, Apr. 30, 1966, pp. 3829–3831.

Yozo Ohtsuka, "Study on Oxazolopyrimidines. I. Synthesis and Spectroscopic Properties of 7–Aminooxazolo[5,4–d] pyrimidines", Segami Chem. Research Cntr., Ohnuma, Sagamihara, Jan. 1970, pp. 187–191.

Yozo Ohtsuka, "Study on Oxazolopyrimidines. V. Preparation of 9–Substituted Hypoxanthines via 7–Aminooxazolo [5,4–d]pyrimidines," Sagami Chem., Research Cntr., Sagamihara, Kanagawa, Dec., 1970, pp. 3909–3913.

Roland K. Robins et al, "Studies on Condensed Pyrimidine Systems. XII. Synthesis of Some 4–n and 2,4–Substituted Pyrido[2,3–d]pyrimidines," Contribution from the Wellcome Research Labs., vol. 77, pp. 2256–2260, Nov. 16, 1954.

Youichi Nunokawa et al, "Expression of Human Inducible Nitric Oxide Synthase Is Regulated by both Promoter and 3'–Regions," Biochemical and Biophysical Research Comm., vol. 233, pp. 523–526 (1997), Article No. RC976471.

Laura C. Green et al, "Analysis of Nitrate, Nitrite, and [$^{15}$N]Nitrate in Biological Fluids," Analytical Biochemistry, vol. 126, pp. 131–138, 1982.

NF-κB INHIBITOR COMPRISING AN INDAN DERIVATIVE AS AN ACTIVE INGREDIENT

This application is a continuation of International Application No. PCT/JP99/03938, with an international filing date of Jul. 22, 1999, now abandoned, which application was not published in English. The international application claimed priority to Japanese Application No. 10-206929, filed in Japan on Jul. 22, 1998.

TECHNICAL FIELD

The present invention relates to indan derivatives and pharmaceutically acceptable salts thereof, as well as NF-κB inhibitors. More specifically, the present invention relates to preventive or therapeutic agents for diseases caused by the activation of NF-κB, said agent having as an active ingredient an indan derivative or a pharmaceutically acceptable salt thereof.

BACKGROUND ART

Nitric oxide (NO) is biosynthesized from L-arginine as a substrate by NO synthase (NOS). Currently three isozymes of NOS have been found: a brain isozyme (bNOS), an endothelial isozyme (eNOS), and an inducible isozyme (iNOS) (Moncada, S. and Higgs, A. (1993) N. Engl. J. Med. 329: 2002–2012). The gene of iNos is induced by endotoxins and cytokines on macrophages, vascular smooth muscle cells, hepatocytes, chondrocytes, gliacytes, etc. and then its expression comes to be observed (Forstermann, U., Gath, I., Schwarz, P., Closs, E. I. and Kleinert, H. (1995) Biochem. Pharmacol. 50: 1321–1332).

The iNOS has been reported to be induced by inflammatory conditions regardless of the species, and the suppression of the enzymatic activity and the expression has been shown to be useful for amelioration of the disease states (Cattell, V. and Jansen, A. (1995) Histochem. J. 27: 777–784; Nussler, A. K. and Billiar, T. R. (1993) J. Leukoc. Biol. 54: 171–178).

It has been reported that arginine derivatives or aminoguanidine exhibit pharmacological effects in model animals of myocarditis, cerebral infarction, arthritis, sepsis, multiple sclerosis, systemic lupus erythematosus, and insulin-dependent diabetes mellitus (Moncada, S. and Higgs, E. A. (1995) Faseb. J. 9: 1319–1330). Though L-N-monomethyl arginine, a NOS inhibitor, is highly toxic at high doses, it not only improves low blood pressure in sepsis but has a marked preventive effect, on which a clinical trial is under way (Moncada, S. and Higgs, E. A. (1995) Faseb. J. 9: 1319–1330).

Furthermore, resistance against sepsis or inflammation induced by carrageenin has been shown in experiments using knockout mice of iNOS, revealing that the expression of iNOS causes these pathological states (Wei, X. Q., Charles, I. G., Smith, A., Ure, J., Feng, G. J., Huang, F. P., Xu, D., Muller, W., Moncada, S. and Liew, F. Y. (1995) Nature 375: 408–411).

An excess of NO produced by the induction of iNOS expression is believed to damage normal cells and cause various disease states. On the other hand, the constitutively occurring NOS (cNOS) termed eNOS or bNOS is required to suppress an increase in blood pressure and to maintain it. Thus, inhibitors that do not inhibit the activity of cNOS and that inhibit iNOS specifically are required. However, since the regions of the proteins that regulate the enzymatic activity of isozymes are very similar to one another in the primary structure, no NOS inhibitors have yet been found which are sufficiently specific (Ogden, J. E. and Moore, P. K. (1995) Trends Biotechnol. 13: 70–78, Manning, R., Jr., Hu. L., Mizelle, H. L., Montani, J. P. and Norton, M. W. (1993) Hypertension 22: 40–48).

As enzyme inhibitors, L-arginine (and amino acid) derivatives have mainly been developed but many of them are low in isozyme specificity. Although aminoguanidine and amidine derivatives, though weakly effective, have been reported to have relatively iNOS-specific inhibitory effects (Southan, G. J. and Szabo, C. (1996) Biochem. Pharmacol. 51: 383–394), pharmaceutical agents having adequate specificity have yet not to be found.

On the other hand, TNF-α, a cytokine produced by various cells including macrophage, is believed to be an important mediator of inflammation (Vassalli, P. (1992) Annu. Rev. Immunol. 10: 411–452). There is growing evidence that the excessive production of TNF-α damages normal cells and causes various pathological conditions (Muto, Y., Nouri-Aria, K. T., Meager, A., Alexander, G. J., Eddleston, A. L. and Williams, R. (1988) Lancet 2: 72–74, Sharief, M. R. and Hentges, R. (1991) N. Engl. J. Med. 325; 467–472).

Increases in TNF-α have been observed in the synovial fluid and the blood of patients with, for example, rheumatoid arthritis (Tetta, C., Camussi, G., Modena, V., Di Vittorio C. and Baglioni, C. (1990) Ann. Rheum. Dis 49: 665–667; Venn, G., Nietfeld, J. J., Duits, A. J., Brennan, F. M., Arner, E., Covington, M., Billingham, M. E. and Mardingham, T. E. (1993) Arthritis Rheum. 36: 819–826). Antibody against TNF-α has also been demonstrated to be effective in clinical trials (Elliott, M. J., Maini, R. N., Feldmann, M., Long-Fox, A., Charles, P., Bijl, H. and Woody, J. N. (1994) Lancet 344: 1125–1127; Elliott, M. J., Maini, R. N., Feldmann, M., Kalden. J. R., Antoni, C., Smolen, J. S., Leeb, B., Breedveld, F. C., Macfarlane, J. D., Bijl, H. and et al. (1994) Lancet 344: 1105–1110; Rankin, E. C., Choy, E. H., Kassimos, D., Kingsley, G. H., Sopwith, A. M., Isenberg, D. A. and Panayi, G. S. (1995) Br. J. Rheumatol. 34: 334–342).

Furthermore, the involvement of TNF-α in sepsis or inflammatory bowel diseases has been pointed out and the ameliorating effects of anti-TNF-α antibody on these diseases have been observed (Vincent, J. L., Bakker, J., Marecaux, G., Schandene, L., Kahn, R. J. and Dupont, E. (1992) Chest 101: 810–815; Hinshaw, L. B., Tekamp-Olson, P., Chang, A. C., Lee, P. A., Taylor, F., Jr., Murray, C. K., Peer, G. T., Emerson, T., Jr., Passey, R. B. and Kuo, G. C. (1990) Circ. Shock 30: 279–292).

These findings expressly indicate that the excessive production of TNF-α causes and aggravates various inflammations, therefore the development of pharmaceutical agents that can inhibit the production of TNF-α (Nyman, U., Mussener, A., Larsson, E., Lorentzen, J. and Klareskog, L. (1997) Clin. Exp. Immunol. 108: 415–419) is required.

Thus, iNOS or TNF-α have been recognized to be one of the causes of various inflammations. However, the fact that many other mediators have been demonstrated to cause inflammation and thereby the cause of the diseases cannot be attributed to any one particular mediator makes the development of therapeutic agents difficult. Under these circumstances, there is a great need for low molecular weight compounds that not only suppress the expression of particular proteins but inhibit widely the production and expression of proteins involved as causative factor in the inflammation.

NF-κB is a protein that regulates gene expression and is one of the so-called transcription factors. Normal cells, when stimulated with inflammatory cytokines such as interleukin-1 (IL-1) and TNF-α, a lipopolysaccharide, or ultraviolet rays, NF-κB is activated and then it translocates from the cytoplasm into the nucleus where it binds to specific nucleotide sequences on the genomic DNA and thereby become involved in the expression of various genes (Blackwell, T. S. and Christman, J. W. (1997) Am. J. Respir. Cell Mol. Biol. 17: 3–9).

Genes encoding iNOS and TNF-α, though entirely different from one another, have regions to which NF-κB binds on the expression control region of the genomic gene thereof, and there is growing evidence that the activation of NF-κB is important for the expression of these proteins in common (Jongeneel, C. V. (1994) Prog. Clin. Biol. Res. 388: 367–381; Xie, Q. w., Kashiwabara, Y. and Nathan, C. (1994) J. Biol. Chem. 269: 4705–4708; Nunokawa, Y., Oikawa, S. and Tanaka, S. (1996) Biochem. Biophys. Res. Commun. 223: 347–352).

Many genes that are involved in immunological inflammatory reactions under expression control by NF-κB are recognized, in addition to iNOS and TNF-α, ones for inflammatory cytokines such as IL-1, IL-6 and IL-8, as well as cell adhesion factors such as ICAM-1, VCAM-1 and ELAM-1 or the like (Collins, T., Read, M. A., Neish, A. S., Whitley, M. Z., Thanos, D. and Maniatis, T. (1995) Faseb. J. 9: 899–909). Furthermore, it is known that inflammatory cytokines, when bound to receptors, transduce NF-κB-activating signals via various routes, and this fact is believed to be cause that further aggravates inflammation. Thus, the activation of NF-κB in inflammation is understood as an etiological and aggravating matter of diseases (Baeuerle, P. A. and Baichwal., V. R. (1997) Adv. immunol. 65: 111–137).

In recent years, it has also been reported that HIV, HTLV-1, CMV, adenovirus and the like activate NF-κB in the host cell (Dezube, B. J., Pardee, A. B., Beckett, L. A., Ahlers, C. M., Ecto, L., Allen-Ryan, J., Anisowicz, A., Sager, R. and Crumpacker, C. S. (1992) J. Acquir. Immune Defic. Syndr. 5: 1099–1104; Nabel, G. and Baltimore, D. (1987) Nature 326: 711–713; Fazely, F., Dezube, B. J., Allen-Ryan, J., Pardee, A. B. and Ruprecht, R. M. (1991) Blood 77: 1653–1656; Munoz, E. and Israel, A. (1995) Immunobiology 193: 128–136). The activation of NF-κB in turn activates its transcription leading to the progression of viral propagation and infection.

Accordingly, it is possible to suppress altogether the induction of expression of these inflammatory cytokines, genes of adhesion molecules, and viruses by inhibiting the activation of NF-κB, and NF-κB inhibitors are promising as therapeutic agents of such diseases as are caused either directly or indirectly by the activation of NF-κB, specifically various inflammatory diseases, autoimmune diseases and viral diseases, and immunosuppressive agents.

Therapeutic agents currently used for chronic diseases such as rheumatism include steroid hormones such as glucocorticoids, non-steroidal aspirin formulations, and the like. However, glucocorticoids are known to be associated with the appearance of severe side effects such as the aggravation of infectious diseases, onset of peptic ulcer, and central effects, and therefore are not amenable to a long-term administration. Furthermore, although the non-steroidal agents suppress the production of prostaglandins etc., they do not provide curative treatments and they are known to exhibit such side effects as the onset of peptic ulcer and central effects.

It has also been reported in recent years that anti-inflammatory drugs at high doses inhibit the activation of NF-κB (Auphan, N., DiDonato, J. A., Rosette, C., Helmberg, A. and Karin, M. (1995) Science 270: 286–290; Shackelford, R. E., Alford, P. B., Xue, Y., Thai, S. F., Adams, D. O. and Pizzo, S. (1997) Mol Pharmacol. 52: 421–429; Bitko, V., Velazquez, A., Yang, L, Yang, Y. C. and Barik, S. (1997) Virology 232: 369–378). However, due to their diverse pharmacological actions, these compounds have side effects, and therefore the development of safer drugs based on a novel mechanism is required.

As a method of inhibiting the actions of TNF-α, it is thought that the use of antibodies that specifically bind to TNF-α and TNF receptor proteins. However, those are both macromolecule proteins and are not suitable for oral administration.

Currently, several compounds are known as NF-κB inhibitors, including, for example, substituted pyrimidine derivatives (International Patents Publication WO9709315, WO9709325, J. Med. Chem., 41, 413 (1998)), xanthine derivatives (Japanese Unexamined Patent Publication (kokai) No, 9-227561), isoquinoline derivatives (Japanese Unexamined Patent Publication (Kokai) No. 10-87491), and the like. However, truly effective drugs have yet to be found.

Several compounds are known as indan derivatives, including, for example, adenosine derivatives that have the antihypertensive actions (Japanese Unexamined Patent Publication (Kokai) No. 2-184649, J. Med. Chem., 34, 1043 (1991)), adenosine derivatives that have the antiallergic actions (Japanese Unexamined Patent Publication (Kokai) No. 60-193998), quinazoline derivatives that have the antidepressant actions (U.S. Pat. No. 3,470,182), and the like. However, a compound that inhibits the activation of NF-κB have not been known yet.

Furthermore, though heterocyclic compounds that have the effect of inhibiting NO production were published recently (Japanese Unexamined Patent Publication (Kokai) No. 10-87492), they do not address the problem of inhibiting NF-κB activation. Compounds published therein are different from the those of the present invention that are represented by the general formula (I) on the substituents of the pyrimidine ring and the amino groups.

DISCLOSURE OF THE INVENTION

The present invention provides preventive and therapeutic agents for diseases caused by the activation of NF-κB, for example, diseases caused by the excessive production of various inflammatory mediators and viral propagation, by inhibiting the activation of NF-κB. More specifically, it provides therapeutic and preventive agents for diseases that are believed to be caused by the excessive production of NO or TNF-α including, for example, sepsis, osteoarthritis, rheumatoid arthritis, cachexia, multiple organ failure, inflammatory bowel diseases, malaria, acquired immune deficiency syndrome, human T-cell leukemia, meningitis, hepatitis, type II diabetes, multiple sclerosis, Behcet disease, systemic lupus erythematosus; ischemic heart diseases such as myocardial infarction, cerebral ischemic diseases and neurodegenerative diseases such as Alzheimer's disease, and the like.

As a result of intensive studies on substances that inhibit the activation of NF-κB, the present inventors have found that indan derivatives represented by the general formula (I) or pharmaceutically acceptable salts thereof potently inhibit the activation of NF-κB and that they inhibit the production of NO and TNF-α on the gene a level, and thereby have accomplished the present invention.

Thus, the present invention relates to indan derivatives represented by the following the general formula (I):

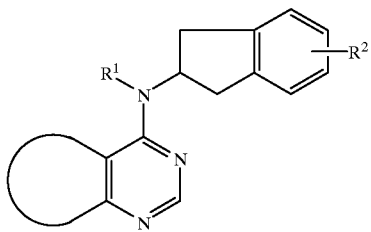

wherein $R^1$ represents a hydrogen atom or an alkyl group having 1 to 4 carbons, and $R^2$ represents a hydrogen atom, a —$OR^3$ group (in the group, $R^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group)], a —$OCOR^4$ group [in the group, $R^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group)], a —$COOR^5$ group [in the group, $R^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group)], a —$CONR^6R^7$ group [in the group, $R^6$ and $R^7$, which may be the same or different, each represent a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), or $R^6$ and $R^7$, together with the nitrogen atom to which they are attached, represent a heterocyclic group that may further contain a nitrogen atom, an oxygen atom, or a sulfur atom], or a —CH=CHR$^8$ group (in the group, $R^6$ represents an alkyl group having 1 to 4 carbons, or an optionally substituted phenyl group), and

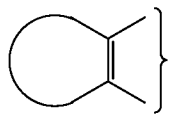

represents a skeleton selected from the group consisting of

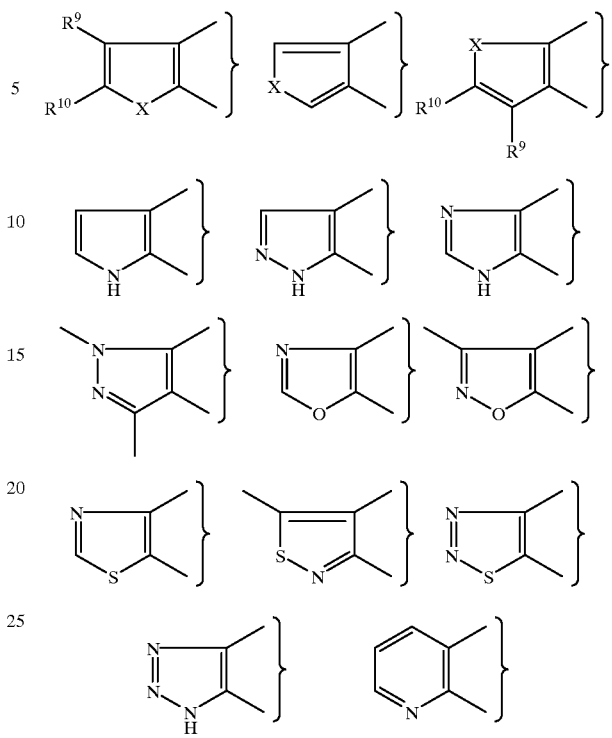

wherein $R^9$ and $R^{10}$, which may be the same or different, each represent a hydrogen atom, a halogen atom, a nitro group, a cyano group, a hydroxy group, an optionally substituted amino group, an optionally esterified or amidated carboxyl group, an alkyl group having 1 to 4 carbons, an alkyloxy group having 1 to 4 carbons, an optionally substituted phenyl group, an optionally substituted aralkyl group having 7 to 11 carbons, or an optionally substituted heterocyclic group, or $R^9$ and $R^{10}$ together form

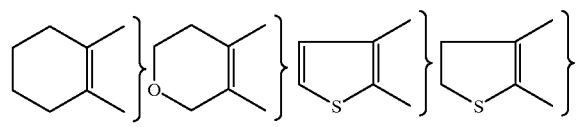

and X represents an oxygen atom or a sulfur atom; pharmaceutically acceptable salts thereof, NF-κB inhibitors, inhibitors of TNF-α production, and inhibitors of NO production containing them as active ingredients, and uses thereof as preventive or therapeutic agents of inflammatory diseases, autoimmune diseases, and viral diseases and/or immunosuppressive agents.

EMBODIMENT FOR CARRYING OUT THE INVENTION

Figure 1:
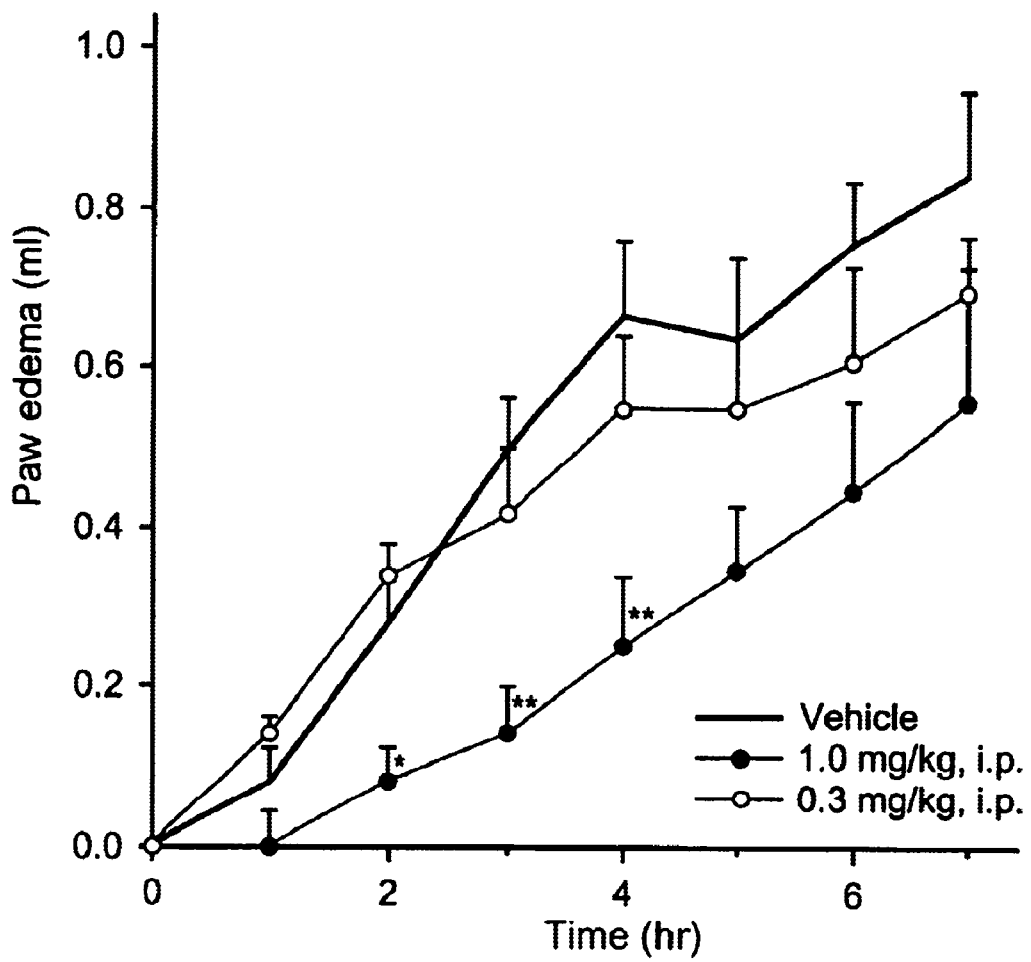
FIG. 1 is a graph showing the result of Experiment 4 in which the compounds of Example 32 were studied using rat models of carageenin foot pad edema. Each point represents the mean±SE (n=5). Dunnett's test was carried out and the results are shown by * p<0.05 and ** p<0.01.

NF-κB inhibitors and inhibitors of TNF-α production are used as agents for suppressing gene expression of one or more substances selected from the group consisting of IL-1, TNF-α, IL-2, IL-6, IL-8, iNOS, granulocyte colony-stimulating factor, interferon-β, ICAM-1, VCAM-1, ELAM-1, major histocompatibility system class I, major histocompatibility system class II, β2-microglobulin, immunoglobulin light chain, serum amyloid A, angiotensinogen, complement B, complement C4, c-myc, HIV, HTLV-1, SV40, CMV, and adenovirus.

There are also provided preventive or therapeutic agents comprising an indan derivative represented by the general formula (I) or a pharmaceutically acceptable salt thereof as an active ingredient for diseases caused by the activation of NF-κB, diseases caused by the excessive production of TNF-α, and diseases caused by the excessive production of NO.

As pharmaceutically acceptable salts, there may be mentioned, for example, a salt with an inorganic acid such as hydrochloric acid, nitric acid, sulfuric acid, phosphoric acid and hydrobromic acid, an organic acid such as maleic acid, fumaric acid, tartaric acid, lactic acid, citric acid, acetic acid, methanesulfonic acid, p-toluene sulfonic acid, adipic acid, palmitic acid and tannic acid, an inorganic metal including an alkaline metal such as lithium, sodium and potassium, and an alkaline earth metal such as calcium and magnesium, and a basic amino acid such as lysine, or a salt with an organic amine such as ammonium.

In the formula, $R^1$ represents a hydrogen atom or an alkyl group having 1 to 4 carbons. Preferred examples of the alkyl group include straight or branched saturated aliphatic hydrocarbon groups having 1 to 4 carbons such as methyl, ethyl, propyl, isopropyl, butyl, isobutyl, sec-butyl, tert-butyl, and saturated alicyclic hydrocarbon groups such as cyclopropyl and cyclobutyl, and a cyclopropyl methyl group. Preferred examples are those in which $R^1$ is a hydrogen atom, a methyl group, or an ethyl group.

As $R^2$, there can be mentioned a hydrogen atom, a —$OR^3$ group [in the group, $R^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], a —$OCOR^4$ group [in the group, $R^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], a —$COOR^5$ group [in the group, $R^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], a —$CONR^6R^7$ group [in the group, $R^6$ and $R^7$, which may be the same or different, each represent a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group), or $R^6$ and $R^7$, together with the nitrogen atom to which they are attached, represent a heterocyclic group that may further contain a nitrogen atom, an oxygen atom or a sulfur atom], or a —CH=$CHR^8$ group (in the group, $R^8$ represents an alkyl group having 1 to 4 carbons, or an optionally substituted phenyl group).

Specifically, as $R^3$, $R^4$, $R^5$, $R^6$ and $R^7$ that are alkyl groups having 1 to 7 carbons, there can be mentioned straight or branched saturated aliphatic hydrocarbon groups having 1 to 7 carbons such as methyl, ethyl, propyl, isopropyl, butyl, isobutyl, sec-butyl, tert-butyl, pentyl, isopentyl, neopentyl, tert-pentyl, hexyl, 3,3-dimethylbutyl, 2-ethylbutyl, 2-methylpentyl, 3-methylpentyl, 4-methylpentyl and heptyl; saturated alicyclic hydrocarbon groups such as cyclopropyl, cyclobutyl, cyclopentyl, cyclohexyl and cycloheptyl; and saturated alicyclic hydrocarbon-aliphatic hydrocarbon groups such as cyclopropylmethyl, cyclopropylethyl, cyclobutylmethyl, cyclopentylmethyl and cyclohexylmethyl, and the like.

As a bicyclic unsaturated or partially saturated hydrocarbon ring group having 9 to 11 carbons, there can be mentioned indene, indan, naphthalene, 1,2-dihydronaphthalene, 1,2,3,4-tetrahydronaphthalene, and the like.

As an aralkyl group having 7 to 11 carbons, there can be mentioned benzyl, phenethyl, 1-phenylethyl, 3-phenylpropyl, 4-phenylbutyl, 5-phenylpentyl, 1-naphtylmethyl, 2-naphtylmethyl, and the like.

A phenyl group, a bicyclic unsaturated or partially saturated hydrocarbon ring group having 9 to 11 carbons, and an aralkyl group having 7 to 11 carbons may be substituted on the ring with one to two substituents selected from;

a hydroxyl group;

a carboxyl group;

an amino group;

a halogen atom such a chlorine atom and a fluorine atom;

an alkyl group preferably having 1 to 4 carbons such as a methyl group, an ethyl group and a propyl group;

an aralkyl group preferably having 7 to 11 carbons such as a benzyl group, a phenethyl group and a 3-phenylpropyl group, and a phenyl group;

an alkyloxy group preferably having 1 to 4 carbons such as a methoxy group, an ethoxy group and a propyloxy group;

an aralkyloxy group preferably having 7 to 11 carbons such as a benzyloxy group, a phenethyloxy group, and a 3-phenylpropyloxy group, and a phenoxy group;

an alkyloxycarbonyl group preferably having 2 to 5 carbons such as a methoxycarbonyl group, an ethoxycarbonyl group and a propyloxycarbonyl group;

an aralkyloxycarbonyl group preferably having 8 to 12 carbons such as a benzyloxycarbonyl group, a phenethyloxycarbonyl group and a 3-phenylpropyloxycarbonyl group, and a phenoxycarbonyl group;

an amino group substituted with one substituent or a combination of two same or different substituents selected from an alkyl group preferably having 1 to 4 carbons such as a methyl group, an ethyl group and a propyl group, an aralkyl group preferably having 7 to 11 carbons such as a benzyl group, a phenethyl group and a 3-phenylpropyl group, and a phenyl group; or a carbamoyl group having an amino group substituted with one substituent or a combination of two same or different substituents selected from an alkyl group preferably having 1 to 4 carbons such as a methyl group, an ethyl group and a propyl group, an aralkyl group preferably having 7 to 11 carbons such as a benzyl group, a phenethyl group and a 3-phenylpropyl group, and a phenyl group, or a cyclic amino group such as a 5- to 8-membered heterocyclic group that may contain 1 to 3 heteroatoms selected from a nitrogen atom, an oxygen atom and a sulfur atom, for example, a group of pyrrolidine, piperidine, morpholine, thiomorpholine and piperazine.

As a heterocyclic group represented by A, there can be mentioned a 5 to 10-membered monocyclic or bicyclic unsaturated, partially saturated or a fully saturated heterocyclic group having 1 to 3 heteroatoms selected from a nitrogen atom, an oxygen atom and a sulfur atom, for example, a group of pyrrole, furan, thiophene, pyran, indole, benzofuran, benzothiophene, benzopyran, pyrazole, isoxazole, isothiazole, indazole, benzisoxazole, benzisothiazole, imidazole, oxazole, thiazole, benzimidazole, benzoxazole, benzothiazole, pyridine, quinoline, isoquinoline, pyridazine, pyrimidine, pirazine, cinnoline, phthalazine, quinazoline, quinoxaline, and a partially or fully saturated ring thereof.

As preferred examples of a heterocyclic group formed from $R^6$ and $R^7$, together with the nitrogen atom to which they are attached, and which may further contain a nitrogen atom, an oxygen atom or a sulfur atom, there can be mentioned a 5- to 8-membered heterocyclic group, for example, a group of pyrrolidine, piperidine, morpholine, thiomorpholine, homopiperidine, piperazine and homopiperazine.

As $R^8$ that is an alkyl group having 1 to 4 carbons and a substituent of an optionally substituted phenyl group, there can be mentioned one described above for $R^3$, $R^4$, $R^5$, $R^6$ and $R^7$.

As

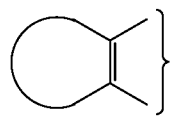

there can be mentioned

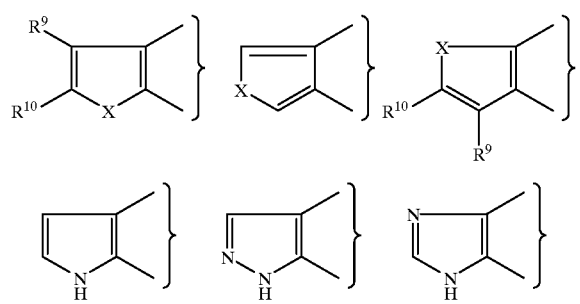

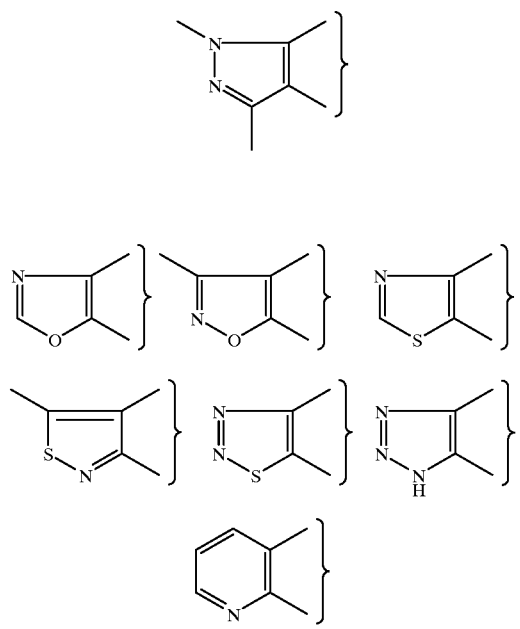

wherein $R^9$ and $R^{10}$, which may be the same or different, each represent a hydrogen atom, a halogen atom, a nitro group, a cyano group, a hydroxy group, an optionally substituted amino group, an optionally esterified or amidated carboxyl group, an alkyl group having 1 to 4 carbons, an alkyloxy group having 1 to 4 carbons, an optionally substituted phenyl group, an optionally substituted aralkyl group having 7 to 11 carbons, or an optionally substituted heterocyclic group, or $R^9$ and $R^{10}$ together form

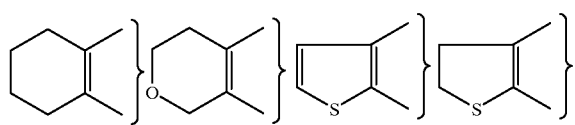

and X represents an oxygen atom or a sulfur atom.

As $R^9$ and $R^{10}$ that are a halogen atom, there can be mentioned a fluorine atom, a chlorine atom, a bromine atom, and the like.

As an optionally substituted amino group, in addition to a non-substituted amino group, there can be mentioned an amino group substituted with one substituent or a combination of two same or different substituents selected from an alkyl group preferably having 1 to 4 carbons such as a methyl group, an ethyl group and a propyl group, an aralkyl group preferably having 7 to 11 carbons such as a benzyl group, and a phenyl group, or a cyclic amino group such as a 5- to 8-membered heterocyclic group that may contain 1 to 3 heteroatoms selected from a nitrogen atom, an oxygen atom and a sulfur atom, for example, a group of pyrrolidine, piperidine, morpholine, thiomorpholine and piperazine, and the like.

As an optionally esterified or amidated carboxyl group, in addition to the carboxyl group, there can be mentioned an alkyloxy carbonyl group preferably having 2 to 5 carbons such as a methoxycarbonyl group, a ethoxycarbonyl group and a propyloxycarbonyl group, an aralkyloxycarbonyl group preferably having 8 to 12 carbons such as a benzyloxycarbonyl group, and a phenoxycarbonyl group; a carbamoyl group having, an amino group, an amino group substituted with a substituent or a combination of two same or different substituents selected from an alkyl group preferably having 1 to 4 carbons such as a methyl group, an ethyl group and a propyl group, and an aralkyl group preferably having 7 to 11 carbons such as a benzyl group and a phenyl group, or an cyclic amino group such as a 5- to 8-membered heterocyclic group that may contain 1 to 3 heteroatoms selected from a nitrogen atom, an oxygen atom and a sulfur atom, for example, a group of pyrrolidine, piperidine, morpholine, thiomorpholine and piperazine.

As an alkyl group having 1 to 4 carbons, there can be mentioned one described above for $R^1$.

As an alkyloxy group having 1 to 4 carbons, there can be mentioned a methoxy group, an ethoxy group, a propyloxy group, an isopropyloxy group, a butyloxy group, and the like.

As an optionally substituted phenyl group and an optionally substituted aralkyl group having 7 to 11 carbons, there can be mentioned one described above for $R^3, R^4, R^5, R^6$ and $R^7$.

As an optionally substituted heterocyclic group, there can be mentioned one described above for A, which may further contain, on the ring, a substituent such as a halogen atom, an alkyl group having 1 to 4 carbons, and an alkyloxy group having 1 to 4 carbons described above for $R^9$ and $R^{10}$, for example furan, thiophane and 3-methylpyridine, and the like.

The present invention specifically provides an indan derivative in which $R^2$ represents a hydrogen atom or a pharmaceutically acceptable salt thereof.

The present invention also provides the above indan derivative in which $R^2$ represents a —$OR^3$ group [in the group, $R^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], or a pharmaceutically acceptable salt thereof.

The present invention also provides the above indan derivative in which $R^2$ represents a —$OCOR^4$ group [in the group, $R^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], or a pharmaceutically acceptable salt thereof.

The present invention also provides the above indan derivative in which $R^2$ represents a —$COOR^5$ group [in the group, $R^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], or a pharmaceutically acceptable salt thereof.

The present invention also provides the above indan derivative in which $R^2$ represents a —$CONR^6R^7$ group [in the group, $R^6$ and $R^7$, which may be the same or different, each represent a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group), or $R^6$ and $R^7$, together with the nitrogen atom to which they are attached, represent a heterocyclic group that may further contain a nitrogen atom, an oxygen atom or a sulfur atom], or a pharmaceutically acceptable salt thereof.

The present invention also provides the above indan derivative in which $R^2$ represents a —$CH=CHR^8$ group (in the group, $R^8$ represents an alkyl group having 1 to 4 carbons, or an optionally substituted phenyl group), or a pharmaceutically acceptable salt thereof.

As specific compounds of the present invention, there can be mentioned the following indan derivatives or pharmaceutically acceptable salts thereof:

4-(2-indanylamino)-5-methylthieno[2,3-d]pyrimidine;
4-(2-indanylamino)thieno[3,4-d]pyrimidine;
4-(2-indanylamino)-7-methylthieno[3,2-d]pyrimidine;
4-(2-indanylamino)pyrrolo[2,3-d]pyrimidine;
4-(2-indanylamino)thieno[2,3-d]pyrimidine;
4-(2-indanylamino)furo [2,3-d]pyrimidine;
4-(2-indanylamino)pyrazolo[3,4-d]pyrimidine;
7-(2-indanylamino)-u-triazolo[4,5-d]pyrimidine;
7-(2-indanylamino)oxazolo[5,4-d]pyrimidine;
3-methyl-4-(2-indanylamino)isoxazolo[5,4-d]pyrimidine;
7-(2-indanylamino)thiazolo[5,4-d]pyrimidine;
2-(2-indanylamino)-1-thia-2,3,5,7-tetraazaindene;
6-(2-indanylamino)-7-methylisothiazolo[3,4-d]pyrimidine;
7-(2-indanylamino)-1,3-dimethyl-1H-pyrazolo[4,3-d] pyrimidine;
4-(2-indanylamino)pyrido[2,3-d]pyrimidine;
4[N-(2-indanyl)-N-methylamino]-5-methylthieno[2,3-d] pyrimidine;
4-(2-indanylamino)-5-phenylthieno[2,3-d]pyrimidine;
4-(2-indanylamino)-5-(2-thienyl)thieno[2,3-d]pyrimidine;
5-(2-furyl)-4-(2-indanylamino)thieno[2,3-d]pyrimidine;
4-(2-indanylamino)-5,6-dimethylthieno[2,3-d]pyrimidine;
4-(2-indanylamino)-5-[6-(3-methylpyridyl)]thieno[2,3-d] pyrimidine;
4-(2-indanylamino)-5-isopropylthieno[2,3-d]pyrimidine;
4-(5-methoxyindan 2-yl)amino5-methylthieno[2,3-d] pyrimidine;
4-(5-hydroxyindan-2-yl)amino-5-methylthieno[2,3-d] pyrimidine;
4-(5-phenoxyindan-2-yl)amino-5-methylthieno[2,3-d] pyrimidine;
4-[5-[(E)-2-(4-methylphenyl)ethenyl]indan-2-yl]amino-5-methylthieno[2,3-d]pyrimidine;
4-(5-methoxycarbonylindan-2-yl)amino-5-methylthieno[2,3-d]pyrimidine;
4-(5-carboxyindan-2-yl)amino-5-methylthieno[2,3-d] pyrimidine sodium salt;
N-propyl-2-(5-methylthieno[2,3-d]pyrimidine-4-yl)amino-5-indancarboxamide;
N-phenyl-2-(5-methylthieno[2,3-d]pyrimidine-4-yl)amino-5-indancarboxamide;
N-benzyl-2-(5-methylthieno[2,3-d]pyrimidine-4-yl)amino-5-indancarboxamide;
2-[5-methylthieno[2,3-d]pyrimidine-4-yl]aminoindan-5-carboxylic acid morpholinamide;
4-(4-methoxyindan-2-yl)amino-5-methylthieno[2,3-d] pyrimidine;
4-(4-methoxycarbonylindan-2-yl)amino-5-methylthieno[2,3-d]pyrimidine;

4-(5-acetoxyindan-2-yl)amino-5-methylthieno[2,3-d]pyrimidine;
4-(5-benzoyloxyindan-2-yl)amino-5-methylthieno[2,3-d]pyrimidine;
6-(2-indanylamino)purine; and
4-(2-indanylamino)thieno[3,2-d]pyrimidine.

An indan derivative represented by the general formula (I) that is used as an active ingredient of the present invention may be prepared by methods described in, for example, Japanese Unexamined Patent Publication (Kokai) No. 5-310743, Japanese Unexamined Patent Publication (Kokai) No. 5-310748, J. Am Chem. Soc., 76, 6073 (1954), J. Am. Chem. Soc., 78,784 (1956), J. Am. Chem. Soc., 88,3829 (1966), J. Org. Chem., 26,4961 (1961), J. Org. Chem., 29,2116 (1964), Chem. Pharm. Bull., 16,750 (1968), J. Chem. Soc.(C), 1856 (1967), Angew. Chem., internat. Edit., 6,83 (1967), Arch. Pharm. Ber. Dtsch. Pharm. Ges., 301,611 (1968), J. Med. Chem., 31,454 (1988), J. Heterocyclic Chem., 30,509 (1993), and the like, and methods based on these.

Method 1

An indan derivative represented by the general formula (I) may be prepared by a method shown, for example, in Scheme 1.

represents an alkyl group having 1 to 4 carbons, preferably methyl or ethyl) with an aminoindan derivative represented by formula (3) ($R^2$ has the same meaning as the general formula (I)) or a salt thereof under a basic condition gives, via an imine product (4), an indan derivative represented by formula (5) ($R^2$ has the same meaning as the general formula (I)) by Dimroth rearrangement. The reaction temperature is preferably 80° C. to 140° C.

It is also possible to prepare an indan derivative represented by formula (5) ($R^2$ has the same meaning as the general formula (I)), without isolating the iminoether (2), by carrying out the following step 2 and step 3 in the absence of solvents.

By alkylating the amino group of the indan derivative represented by formula (5) ($R^2$ has the same meaning as the general formula (I)) thus obtained, an indan derivative represented by formula (6) ($R^{1'}$ represents an alkyl group having 1 to 4 carbons and $R^2$ has the same meaning as the general formula (I)) can be prepared (step 4). As a method of alkylation, there can be applied a nucleophilic displacement reaction of a halogenated alkyl, an alkylsulfonate ester and an alkysulfate, or a reductive alkylation in which the corresponding aldehyde or ketone is reacted in the presence Scheme 1

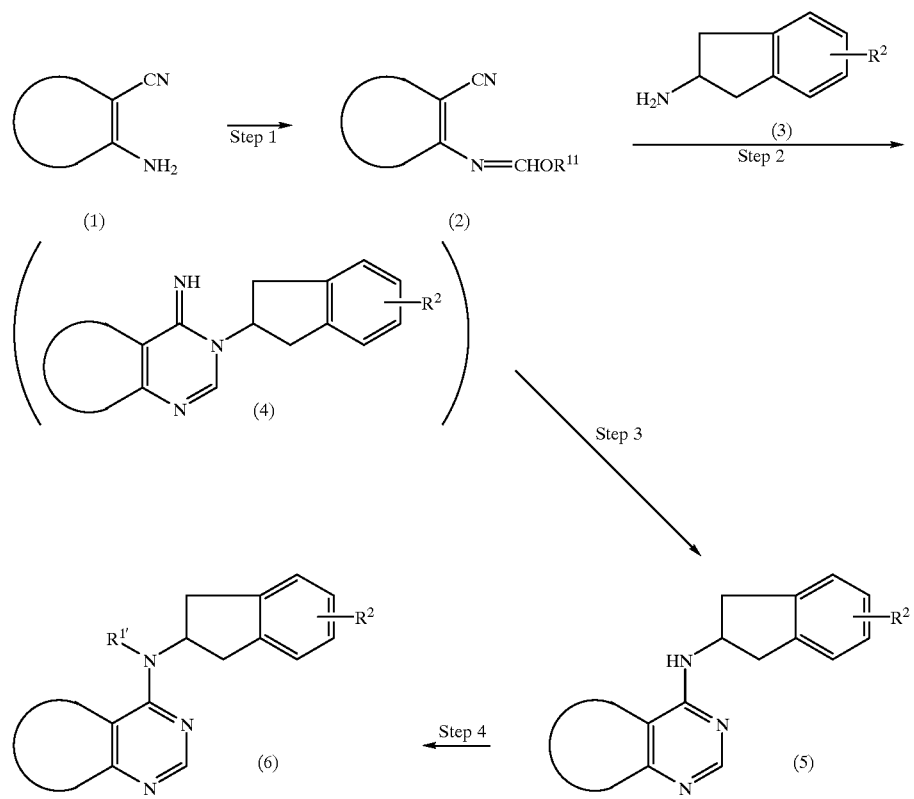

First, aminonitrile (1) is condensed with an orthoester such as trimethyl orthoformate or triethyl orthoformate to yield an iminoether (2) ($R^{11}$ represents an alkyl group having 1 to 4 carbons, preferably methyl or ethyl) (step 1). In some instances, this reaction is conducted in the presence of acetic anhydride. Reaction of the iminoether (2) ($R^{11}$ of a reducing agent such as sodium borohydride or sodium cyanoborohydride.

Method 2

The indan derivative of formula (5) ($R^2$ has the same meaning as the general formula (I)) may also be synthesized by the method shown in Scheme 2.

Scheme 2

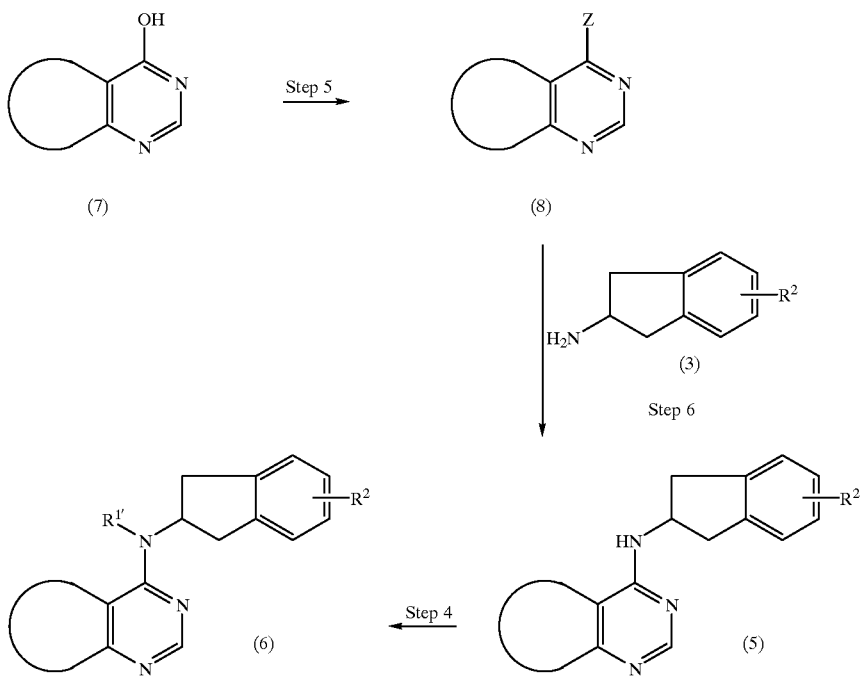

First, a 4-substituted pyrimidine derivative represented by formula (8) (in the formula, Z represents a leaving group, preferably a chlorine atom or a methylthio group) is synthesized from a 4-hydroxypyrimidine derivative represented by formula (7) (step 5). For example, the compound represented by formula (8) in which Z is a chlorine atom can be synthesized by heating formula (7) with phosphorus oxychloride or thionyl chloride in the presence or absence of a base such as diethyl aniline. The compound represented by formula (8) in which Z is a methylthio group can also be synthesized by reacting formula (7) with diphosphorus pentasulfide, followed by methyl iodide in the presence of a base such as sodium hydroxide.

Formula (8) (in the formula, Z represents a leaving group, preferably a chlorine atom or a methylthio group) thus obtained is aminated with an aminoindan derivative represented by formula (3) ($R^2$ has the same meaning as the general formula (I)) or a salt thereof in the presence or absence of a base such as triethylamine at a reaction temperature of room temperature to 180° C. to yield an indan derivative of formula (5) ($R^2$ has the same meaning as the general formula (I)) (step 6). The reaction is carried out in the absence of a solvent or preferably in a non-reactive solvent such as ethanol.

The alkylation of the amino group of the indan derivative represented by formula (5) ($R^2$ has the same meaning as the general formula (I)) thus obtained may be conducted by the method described above (step 4).

The aminoindan derivative (3) to be used as a starting material for synthesis of the compounds of interest by these methods can be prepared in the following synthetic method according to and based on the methods described in Japanese Unexamined Patent Publication (Kokai) No. 63-23853, J. Med. Chem., 25,1142 (1982), J. Med. Chem., 33,703 (1990), Synthesis, 285 (1995), Chem. Rev., 95,2457 (1995), J. Org. Chem., 58,2201 (1993), Synthesis, 47 (1989), J. Am Chem. Soc., 90,5616 (1968), J. Am Chem. Soc., 119,7974 (1997), Jikken Kagaku Koza (Experimental Chemistry Series), Vol. 20, Fourth edition, page 187 (1992, Maruzen K.K.), Jikken Kagaku Koza (Experimental Chemistry Series), Vol. 22, Fourth edition, pages 3, 43, and 137 (1992, Maruzen K.K.), and Jikken Kagaku Koza (Experimental Chemistry Series), Vol. 23, Fourth edition, page 7 (1992, Maruzen K.K.).

The α position of the carbonyl group of a ketone derivative represented by the general formula (9):

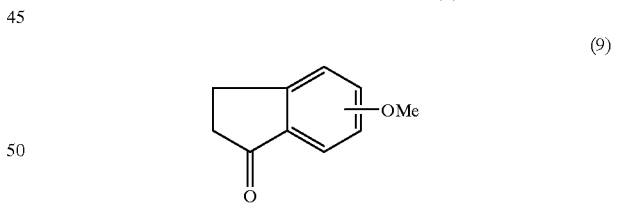

is converted to an oxime using a nitrite ester such as isoamyl nitrite, butyl nitrite and ethyl nitrite, in the presence of an acid catalyst such as hydrochloric acid in a non-reactive solvent such as diethyl ether, ethanol, methanol, tetrahydrofuran, benzene and methylene chloride at room temperature to 60° C. Preferably the reaction is conducted using isoamyl nitrite or hydrochloric acid in methanol at 40° C.

The oxime derivative of the general formula (10) thus obtained:

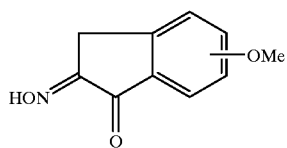

(10)

is subjected to catalytic hydrogenation in acetic acid by adding sulfuric acid or perchloric acid in the presence or absence of palladium chloride with palladium carbon as a catalyst at ordinary pressure or an atmosphere of pressurized hydrogen at a temperature of room temperature to 60° C. to yield an amine derivative of the general formula (11):

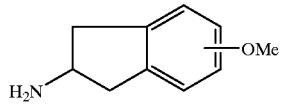

(11)

The amine derivative (11) is then subjected to a demethylation reaction at room temperature or under heating, using boron tribromide, boron trichloride, hydroiodic acid, hydrobromic acid and the like, preferably by heating to reflux, using hydrobromic acid in acetic acid to produce a compound represented by the general formula (12):

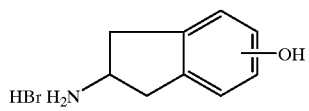

(12)

A compound represented by the general formula (13):

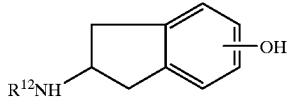

(13)

(wherein $R^{12}$ is a protecting group of an amino group, preferably a tert-butoxycarbonyl group or a benzyloxycarbonyl group) can be synthesized by an introduction reaction of a protecting group into the amino group of compound (12), the method described in Peputido Goseino Kisoto Jikken (the Basic and Experimental Peptide Synthesis), Nobuo Izumiya, Tetsuo Kato, Haruhiko Aoyagi, Michinori Waki, (1985, Maruzen K.K.).

A compound represented by the general formula (14):

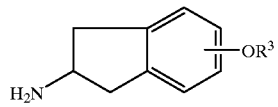

(14)

(wherein $R^3$ has the same meaning as the above) is obtained by etherification and deprotection of the amino protecting group of compound (13). Etherification can be carried out according to the method such as is described in Jikken Kagaku Koza (Experimental Chemistry Series), Vol. 20, Fourth edition, page 187 (1992, Maruzen K.K.). The deprotection reaction of the amino protecting group can also be carried out by a conventionally used method such as the method described in Peputido Goseino Kisoto Jikken (The Basic and Experimental Peptide Synthesis), Nobuo Izumiya, Tetsuo Kato, Haruhiko Aoyagi, Michinori Waki, (1985, Maruzen K.K.), and preferably it is a deprotection reaction by acid or catalytic hydrogenation. When an acid is used in the deprotection reaction, the ether derivative (14) can be prepared as a salt with the acid used.

A compound represented by the general formula (15):

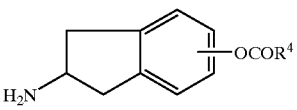

(15)

(wherein $R^4$ has the same meaning as the above) can be obtained by esterification followed by deprotection reaction of the amino protecting group of compound (13).

Esterification can be carried out according to the method such as is described in Jikken Kagaku Koza (Experimental Chemistry Series), Vol. 22, Fourth edition, page 43 (1992, Maruzen K.K.). The deprotection reaction of the amino protecting group can also be carried out by a method similar to the one described above.

A compound represented by the general formula (16):

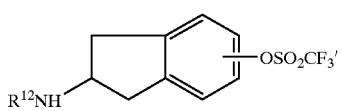

(16)

(wherein $R^{12}$ has the same meaning as the above) is a trifluoromethanesulfonate of a phenolic hydroxy group of compound (13), prepared by using trifluoromethanesulfonic unhydride and pyridine.

A vinyl derivative represented by the general formula (17):

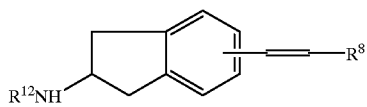

(17)

(wherein $R^8$ and $R^{12}$ have the same meaning as the above) can be prepared by a cross coupling reaction of a trifluoromethanesulfonic ester (16) and a catechol borane derivative represented by the general formula (18):

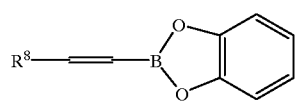

(18)

(wherein $R^8$ has the same meaning as the above) or a boronic acid derivative represented by the general formula (19):

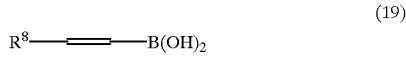

(wherein $R^8$ has the same meaning as the above) using a palladium catalyst and a base. The palladium catalyst as used herein is $Pd(PPh_3)_4$, $PdCl_2(dppf)$ (dppf=1,1'-bis(diphenylphosphino)ferrocene, $Pd(DBA)_2$/diphenyl (2,4,6-trimethoxyphenyl)phosphine (DBA=dibenzalacetone), $Pd(DBA)_2$/bis(2,4,6-trimethoxyphenyl)phenylphosphine, and the like, the base is tripotassium phosphate, potassium carbonate, sodium carbonate, potassium hydroxide, sodium hydroxide, sodium ethoxide, and the like, and the solvent used is tetrahydrofuran, dioxane, dimethylformamide, toluene, benzene, dimethoxyethane, ethanol, and the like.

Furthermore, in order to prevent the decomposition of palladium catalysts, potassium iodide, potassium bromide, lithium chloride, and the like may be added. Preferably, any of the above palladium catalysts is used, any of tripotassium phosphate, potassium carbonate and sodium carbonate is used as the base, any of tetrahydrofuran, dioxane, dimethylformamide and a mixed solvent of toluene and ethanol is used as the solvent, and any of potassium bromide and lithium chloride is used as the additive. Preferred reaction temperature is room temperature to 120° C.

A compound represented by the general formula (20):

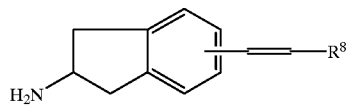

(wherein $R^8$ has the same meaning as the above) can be obtained by removing the amino protecting group of compound (17) with an acid such as trifluoromethanesulfonic acid, methanesulfonic acid, hydrogen bromide, hydrochloric acid, trifluoroacetic acid, and the like, wherein the compound is obtained as a salt with the acid used.

A carboxylic acid represented by the general formula (21);

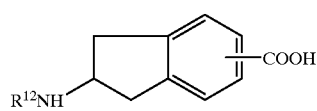

(wherein $R^{12}$ has the same meaning as the above) is synthesized from the compound (17) via 1) the formation of an aldehyde by oxidative cleavage, 2) the oxidation of the aldehyde to a carboxylic acid or carboxylic acid ester, and 3) the hydrolysis of the carboxylic acid ester (when oxidized to the carboxylic acid ester).

In the formation of an aldehyde by oxidative cleavage in 1), preferably an oxidizing agent of osmium tetraoxide and sodium periodate are used, and the reaction is conducted in a mixed solvent of any of organic solvent such as ether, dioxane, acetone, tetrahydrofuran, and water.

In the oxidation in 2), preferably any of manganese dioxide, silver oxide, and argentic oxide (AgO) as the oxidizing agent, an alcohol such as methanol and ethanol as the solvent is used, and the reaction is carried out at room temperature to 50° C. Alternatively, reaction is carried out using sodium chlorite, sodium hydrogen phosphate, isobutylene, or hydrogen peroxide, an aqueous solvent such as tert-butanol/water or acetonitrile/water. When manganese dioxide is used as the oxidizing agent, a carboxylic acid ester corresponding to the alcohol used is formed, which is hydrolyzed in a known method using an alkali to produce a carboxylic acid.

The carboxylic acid is also produced directly by reacting the vinyl derivative (17) with potassium permanganate.

An amide derivative represented by the general formula (22):

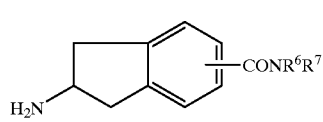

(wherein $R^6$ and $R^7$ have the same meaning as the above) can be prepared by the amidation of the carboxylic acid (21) followed by the deprotection reaction of the amino protecting group. Amidation is carried out using a conventionally used method such as is described in Jikken Kagaku Koza (Experimental Chemistry Series), Vol. 22, Fourth edition, pages 137 (1992, Maruzen K. K.) or Peputido Goseino Kisoto Jikken (The Basic and Experimental Peptide Synthesis), Nobuo Izumiya, Tetsuo Kato, Haruhiko Aoyagi, Michinori Waki, (1985, Maruzen K. K.). The deprotection reaction of the amino protecting group can be carried out in a similar method as described above. When an acid is used in the deprotection reaction, the amide derivative (22) can be prepared as a salt with the acid used.

An ester derivative represented by the general formula (23):

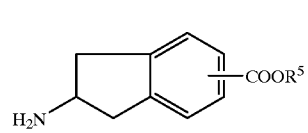

(wherein $R^5$ has the same meaning as the above) can be prepared by the esterification of the carboxylic acid (21) followed by the deprotection reaction of the amino protecting group. The esterification and the deprotection reaction of the amino protecting group can be carried out in a similar general method as described above. When an acid is used in the deprotection reaction, it can be prepared as a salt with the acid used.

A compound represented by the general formula (22):

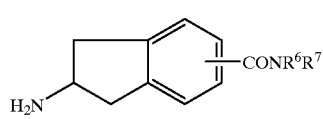

(wherein $R^6$ and $R^7$ have the same meaning as the above), and some of a compound represented by the general formula (23):

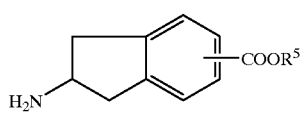

(23)

(wherein $R^5$ has the same meaning as the above) can also be prepared by the following method:

First, an acetyl group is introduced into the benzene ring of a compound (24):

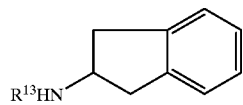

(24)

(wherein $R^{13}$ is a protecting group of an amino group, preferably an acetyl group or a benzoyl group), to be converted to compound (25):

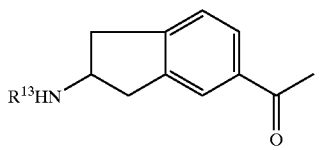

(25)

(wherein $R^{13}$ has the same meaning as the above). The acetylation is preferably carried out using acetyl chloride, acetic anhydrous, or a Lewis acid such as aluminum chloride, iron (III) chloride, and titanium (IV) chloride, and a solvent such as nitrobenzene, carbon disulfide, methylene chloride and ethylene chloride. The acetyl derivative (25) obtained is then reacted with a hypohalite. Preferably, it is reacted with a hypohalite such as sodium hypochlorite or sodium hypobromite at room temperature in a aqueous solvent such as dioxane/water, tetrahydrofuran/water. This produces compound (26):

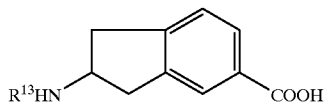

(26)

(wherein $R^{13}$ has the same meaning as the above), and then the protecting group of the amino group is removed with an acid to yield a deprotection derivative (27);

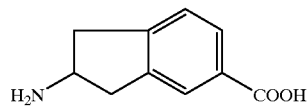

(27)

as a salt with the acid used.

Another protecting group is introduced to the amino group to produce a compound (28):

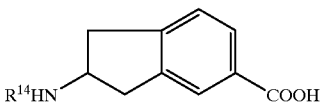

(28)

(wherein $R^{14}$ is, for example, a tert-butoxycarbonyl group or a benzyloxycarbonyl group), which is then esterified and deprotected again to obtain an ester derivative represented by the general formula (29):

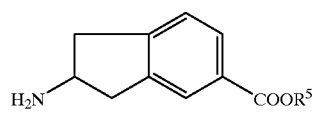

(29)

(wherein $R^5$ has the same meaning as the above), and a salt thereof, or which is then amidated and deprotected again to obtain an amide derivative represented by the general formula (30):

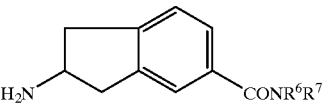

(30)

(wherein $R^6$ and $R^7$ have the same meaning as the above), and a salt thereof. The ester derivative represented by the general formula (29) can also be prepared by heating compound (27) in an alcohol in the presence of thionyl chloride, or an acid such as hydrogen chloride or toluenesulfonic acid.

Compound (I) of the present invention thus obtained can be converted as desired to various salts, and can be purified by means of recrystallization, column chromatography, and the like.

Furthermore, some of the present invention compound (I) have an asymmetric center and these optical isomers are also within the scope of the present invention, and can be obtained as single optical active isomers by separating from the racemates using various methods. Examples of the methods used include;

(1) a method of separation using optically active columns;
(2) a method of using optically active acids to produce a salt, which is then separated by recrystallization;
(3) a method of separation using enzymatic reactions; and
(4) a method of separation using combinations of the above (1) to (3).

Since substances represented by the general formula (I) claimed in the present invention can suppress the activation of NF-κB, they are effective as preventive and therapeutic agents for diseases caused by the activation of NF-κB, for example diseases caused by the excessive production of various inflammatory mediators and viral propagation. More specifically they are useful as therapeutic and preventive agents for diseases caused by the excessive production of NO or TNF-α including, for example, sepsis, osteoarthritis, rheumatoid arthritis, cachexia, multiple organ failure, inflammatory bowel diseases, malaria, acquired immune deficiency syndrome, human T-cell leukemia, meningitis, hepatitis, type II diabetes, multiple sclerosis, Behcet disease, systemic lupus erythematosus, ischemic heart diseases such as myocardial infarction, cerebral ischemic disease, neurodegenerative diseases such as Alzheimer's disease, and the like.

When the compounds of the present invention are used as the above-mentioned pharmaceutical compositions, they can be used orally in the form of tablets, capsules, elixirs, microcapsules, and the like, or parenterally in the form of injections and the like such as solutions or suspensions with water or other pharmaceutically acceptable liquids. For example, they can be prepared by mixing the invention compound with pharmaceutically acceptable carriers, flavoring agents, excipients, stabilizers, and the like in a commonly recognized form. Additives that can be blended into tablets etc. include, for example, binders such as gelatin, swelling agents such as corn starch, excipients such as crystalline cellulose, lubricants such as magnesium stearate, and the like. When formulated into capsules, the above compositions may further include liquid carriers. Aseptic compositions for injection can also be formulated in the conventional manner.

As aqueous solutions for injection, there may be mentioned isotonic solutions that contain glucose etc., and they may be used in combination with suitable solubilizer such as polyethyleneglycol. Buffers, stabilizers, preservatives, antioxidants, soothing agents, and the like may also be blended. The pharmaceutical preparations thus obtained can be administered to mammals including humans. Though the dosage varies depending on the pathologic state etc. the daily dose per human adult, it is, when given orally, generally about 0.01 to 100 mg, preferably about 0.1 to 50 mg, and more preferably about 1.0 to 25 mg. When they are given parenterally, the daily dose per human adult is generally intravenously administered at amounts of about 0.001 to 50 mg, preferably about 0.01 to 25 mg, more preferably about 0.1 to 10 mg.

The inhibitory effect of NF-κB can be examined by detecting the expression of genes regulated by the activation of NF-κB, or by determining directly or indirectly the amount expressed of proteins encoded by the genes.

The effect of suppressing the excessive expression of inflammatory proteins may be examined, as shown in the results of Experimental Examples, by stimulating cells or individual animals with a cytokine such as IL-1 or TNF-α, or a lipopolysaccharide, and then determining directly or indirectly the amount of inflammatory proteins that may be increased in the culture medium or the body fluid.

Also, as methods of confirming in vivo the antiinflammatory effects in its broad sense, the effect of suppressing edema induced by dextran or carrageenin may be determined. It has already been reported that the inhibition of NO and TNF-α production are effective in this model (Filion, M. C. and Phillips, N. C. (1997) Br. J. Pharmacol. 122, 551–557; Tsao, P. W., Suzuki, T., Totsuka, R., Murata, T., Takagi, T., Ohmachi, Y., Fujimura, H. and Takata, I. (1997) Clin. Immunol. Immunopathol. 83, 173–178; Cuzzocrea, S., Zingarelli, B., Hake, P., Salzman, A. L. and Szabo, C. (1998) Free Radic. Biol. Med. 24, 450–459). Furthermore, in specific disease the efficacy, for example as therapeutic agents for sepsis can be evaluated by administering a lipopolysaccharide to animals such as mice and then improving the survival ratio of the animals.

The efficacy as therapeutic agents for rheumatoid arthritis can also be evaluated in animal models of arthritis using adjuvants. When model animals of myocardial infarction are used, DNA having the decoy sequence of NF-κB is shown to suppress the lesion of the infarction (Sawa, Y., Morishita, R., Suzuki, K., Kagisaki, K., Kaneda, Y., Maeda, K., Kadoba, K. and Matsuda, H. (1997) Circulation 96, II-280–284; discussion II-285), and thereby such model animals are also suitable for investigating the efficacy of therapeutic agents for ischemic heart diseases.

Thus the efficacy of NF-κB inhibitors having an activity of inhibiting the production of NO and TNF-α as therapeutic agents can be confirmed using known animal models that can be prepared by a person skilled in the art.

EXAMPLES

The present invention is now explained in further details with reference to following examples.

Preparation Example 1

2-(tert-butoxycarbonylamino)-5-hydroxyindan

Method 1 a) 6-methoxy-1-indanone (8.6 g, 53 mmol) (see J. Org. Chem., 35, 647 (1970)) was added to methanol (500 ml), then heated to 40° C., and isoamyl nitrite (15 ml, 110 mmol) and concentrated hydrochlolic acid (8.5 ml) were added thereto followed by stirring for 2 hours. The crystals that deposited on cooling the reaction mixture were filtered to obtain 6-methoxy-2-oxyimino-1-indanone (5.5 g, 29 mmol) having the following physical properties:

$^1$H NMR (400 MHz, DMSO-d$_6$): δ3.69 (2H, s), 3.83 (3H, s), 7.21 (1H, d, J=2 Hz), 7.32 (1H, dd, J=2 Hz, 8 Hz), 7.53 (1H, d, J=8 Hz), 12.58 (1H, br. s).

b) 6-methoxy-2-oxyimino-1-indanone (5.5 g, 29 mmol) was suspended in acetic acid (85 ml), and palladium carbon (10%, 2.0 g), palladium chloride (60 mg), and concentrated sulfuric acid (4 ml) were added thereto. The mixture was then stirred under a hydrogen atmosphere at 5 kg/cm$^2$ for 6 hours. After the filtrate obtained by filtering the reaction mixture was concentrated under reduced pressure, it was neutralized with 10% sodium hydroxide and extracted with chloroform. After the organic layer was dried over anhydrous sodium sulfate, the solvent was distilled off under reduced pressure to obtain 2-amino-5-methoxyindan as a crude product. This was used as a raw material for the subsequent reaction without further purification.

c) To crude 2-amino-5-methoxyindan were added 30% hydrobromic acid-acetic acid (6.0 ml) and an aqueous solution of 48% hydrobromic acid (4.0 ml), and then the mixture was heated to reflux for 2 hours. The solvent was distilled off under reduced pressure, dioxane and toluene were added thereto, and the solvent was distilled off again. The residue thus obtained was dissolved in dioxane (100 ml) and water (50 ml). The reaction mixture was neutralized with triethylamine (about 10 ml), di-tert-butyl dicarbonate (7.0 g, 32 mmol) was added thereto, and the mixture was stirred at room temperature for 2 hours. To the reaction mixture was added ethyl acetate, the organic layer was washed with an aqueous solution of saturated potassium hydrogensulfate, brine, an aqueous solution of saturated sodium hydrogencarbonate, and then was dried over anhydrous sodium sulfate. The residue obtained by distilling off the solvent under reduced pressure was purified by silica gel chromatography (hexane:ethyl acetate=4:1) to obtain the title compound (2.5 g, 10 mmol) having the following physical properties:

$^1$H NMR (400 MHz, CDCl$_3$): δ1.54 (9H, s), 2.70 (2H, dt, J=5 Hz, 12 Hz), 3.20 (2H, m), 4.43 (1H, br. s), 4.75 (1H, br. s), 5.26 (1H, br. s), 6.64 (1H, dd, J=2 Hz, 18 Hz), 6.69 (1H, s), 7.03 (1H, d, J=8 Hz).

Method 2 a) Using 5-methoxy-1-indanone (5.0 g, 31 mmol) in stead of 6-methoxy-1-indanone, methanol (100 ml), isoamyl nitrite (1.9 ml, 14 mmol) and concentrated hydrochloric acid (1.2 ml), a similar procedure to a) in Method 1 was carried out. The product obtained was purified by silica gel chromatography (hexane:ethyl acetate=3:1) to obtain 5-methoxy-2-oxyimino-1-indanone (4.5 g, 23 mmol) having the following physical properties:

$^1$H NMR (400 MHz, DMSO-$d_6$): δ3.73 (2H, s), 3.89 (3H, s), 7.02 (1H, dd, J=2 Hz, 8 Hz), 7.15 (1H, d, J=2 Hz), 7.69 (1H, d, J=8 Hz), 12.45 (1H, br. s).

b) 5-methoxy-2-oxyimino-1-indanone (440 mg, 2.3 mmol) was suspended in acetic acid (6.5 ml) and palladium carbon (10%, 170 mg), palladium chloride (20 mg), and concentrated sulfuric acid (4.4 ml) were added thereto. A similar procedure to b) in Method 1 was carried out to obtain 2-amino-5-methoxyindan (300 mg) as a crude product. This was used without further purification as a raw material for the subsequent reaction.

c) After crude 2-amino-5-methoxyindan was demethylated using 30% hydrobromic acid-acetic acid (1.8 ml) and an aqueous solution of 48% hydrobromic acid (1.2 ml), a similar procedure to c) in Method 1 was carried out using dioxane (6.2 ml), water (3.1 ml), triethylamine (about 0.55 ml), and di-tert-butyl dicarbonate (440 mg, 2.0 mmol) to obtain the title compound (300 mg, 1.1 mmol).

Preparation Example 2

2-(tert-butoxycarbonylamino)-5-[(E)-2-(4-methylphenyl) ethenyl]indan a) To a solution of 2-(tert-butoxycarbonylamino)-5-hydroxyindan (270 mg, 1.1 mmol) in pyridine (0.5 ml) was added trifluoromethanesulfonic anhydride (360 mg, 1.3 mmol) under ice cooling, and the mixture was stirred at room temperature for 30 minutes. The reaction mixture was diluted with ethyl acetate, and the organic layer was washed with an aqueous solution of saturated potassium hydrogensulfate, brine, an aqueous solution of saturated sodium hydrogencarbonate, and then was dried over anhydrous sodium sulfate. The residue obtained by distilling off the solvent under reduced pressure was purified by silica gel chromatography (hexane:ethyl acetate=4:1) to obtain 2-(tert-butoxycarbonylamino)-5-trifluoromethanesulfonyloxyindan (320 mg, 0.84 mmol) having the following physical properties:

$^1$H NMR (400 MHz, CDCl$_3$): δ1.45 (9H, s), 2.80 (2H, m), 3.30 (2H, m), 4.50 (1H, br. s), 4.70 (1H, br. s), 7.06 (1H, d, J=8 Hz), 7.11 (1H, s), 7.25 (1H, d, J=8 Hz).

IR (KBr): ν3350, 2980, 1680, 1540, 1440, 1250, 1210 cm$^{-1}$.

b) By adding catechol borane (0.50 ml; 4.7 mmol) to 4-ethinyl toluene (540 mg, 4.7 mmol), and stirring the mixture at 70° C. for 2 hours, a catechol borane derivative was obtained as a solid form which was used without purification as a raw material for the subsequent reaction. To the catechol borane derivative (240 mg, 1.0 mmol) was added ice water (5 ml), and then was stirred at room temperature for 2 hours. The reaction mixture was extracted with ethyl acetate, and the organic layer was washed with water and dried over anhydrous magnesium sulfate. The solvent was distilled off under reduced pressure to obtain (E)-2-(4-methylphenyl)ethenylboronic acid (220 mg) as a crude product.

c) 2-(tert-butoxycarbonylamino)-5-trifluoromethane- sulfonyloxyindan (260 mg, 0.69 mmol), (E)-2-(4-methylphenyl)ethenylboronic acid (180 mg), toluene (7 ml), Pd(PPh$_3$)$_4$ (30 mg, 0.026 mmol), 2M sodium carbonate (0.99 ml), ethanol (3.0 ml), and lithium chloride (64 mg, 1.5 mmol) were heated to reflux for 5 hours. The reaction mixture was diluted with ether, washed with water, dried, and then the solvent was distilled off under reduced pressure. The residue obtained was purified by silica gel chromatography (hexane:ethyl acetate=4:1) to obtain the title compound (190 mg, 0.54 mmol) having the following physical properties;

$^1$H NMR (400 MHz, CDCl$_3$): δ1.45 (9H, s), 2.35 (3H, s), 2.80 (2H, m), 3.30 (2H, m), 4.50 (1H, br. s), 4.80 (1H, br. s), 7.04–7.11 (2H, m), 7.16 (3H, m), 7.26–7.31 (2H, m), 7.39 (2H, m).

Preparation Example 3

2-(tert-butoxycarbonylamino)-5-methoxycarbonylindan

A mixture of 2-(tert-butoxycarbonylamino)-5-[(E)-2-(4-methylphenyl)ethenyl]indan (190 mg, 0.54 mmol) synthesized in Preparation Example 2, osmium tetraoxide (on poly (4-vinylpyridine), 140 mg), sodium metaperiodate (450 mg, 2.1 mmol), dioxane (3.8 ml) and water (0.8 ml) was vigorously stirred at room temperature. The reaction mixture was diluted with ethyl acetate, the organic layer was washed with water, dried, and then the solvent was distilled off under reduced pressure to obtain an aldehyde mixture (170 mg).

Subsequently, the aldehyde mixture (170 mg) was dissolved in methanol (7.0 ml), to which sodium cyanide (270 mg, 5.5 mmol), acetic acid (0.10 ml), and manganese dioxide (1.87 g, 22 mmol) were added, and the reaction mixture was stirred at room temperature for 30 minutes. Methanol was added thereto, and the reaction mixture was filtered, concentrated, and after the addition of water, extracted with methylene chloride. The organic layer was dried, and the solvent was distilled off under reduced pressure to obtain a residue, which was purified by silica gel chromatography (hexane:ethyl acetate=4:1) to obtain the title compound (76 mg, 0.26 mmol) having the following physical properties:

$^1$H NMR (400 MHz, CDCl$_3$): δ1.45 (9H, s), 2.82 (2H, m), 3.31 (2H, m), 3.90 (3H, s), 4.49 (1H, br.), 4.72 (1H, br.), 7.27 (1H, m), 7.87 (1H, m), 7.88 (1H, m).

Preparation Example 4

2-(tert-butoxycarbonylamino)-5-carboxyindan

Method 1

2-(tert-butoxycarbonylamino)-5-methoxycarbonylindan (76 mg, 0.26 mmol) synthesized in Preparation Example 3 was dissolved in methanol (2 ml), to which an aqueous solution of 1N sodium hydroxide (0.29 ml, 0.29 mmol) was added and the mixture was heated to reflux for 1.5 hours. After the reaction mixture was diluted with water and washed with ethyl acetate, the aqueous layer was acidified with an aqueous solution of saturated sodium hydrogensulfate and extracted with ethyl acetate. After the organic layer was dried, the solvent was distilled off under reduced pressure to obtain the title compound (58 mg, 0.21 mmol) having the following physical properties:

$^1$H NMR (400 MHz, CDCl$_3$): δ1.45 (9H, s), 2.85 (2H, m), 3.33 (2H, m), 4.50 (1H, br.), 4.75 (1H, br.), 7.30 (1H, m), 7.93 (1H, m), 7.94 (1H, m).

Method 2 a) 2-aminoindan (6.0 g, 45 mmol) was dissolved in dry pyridine (7 ml), to which acetic anhydride (4.5 ml, 47.3 mmol) was added dropwise while cooling in ice water. After the reaction mixture was returned to room temperature and stirred for 20 minutes, water was added. The precipitate that deposited was filtered to obtain 2-acetamidindan (5.6 g, 32 mmol).

b) To a solution of anhydrous aluminum chloride (3.4 g, 25.5 mmol) in 1,2-dichloroethane (20 ml) cooled in ice water was added dropwise acetyl chloride (1.11 ml, 15.5 mmol) under an argon atmosphere. After the addition was complete, a solution of 2-acetamidindan (5.6 g, 32 mmol) in 2-dichloroethane (40 ml) was added. The reaction mixture was allowed to react at room temperature for 2.5 hours, and was cooled again in ice water, to which ice was carefully added and the reaction mixture was extracted with methylene chloride. The organic layer was washed with a 1N potassium hydroxide solution and brine, and dried over anhydrous sodium sulfate. The solvent was distilled off under reduced pressure to obtain 2-acetamide-5-acetylindan (2.1 g, 9.8 mmol) having the following physical properties:

$^1$H NMR (400 MHz, CDCl$_3$): δ1.95 (3H, s), 2.58 (3H, s), 2.82–2.87 (2H, m), 3.32–3.38 (2H, m), 4.77 (1H, m), 5.65 (1H, broad), 7.31 (1H, d, J=7.8 Hz), 7.81 (1H, d, J=7.8 Hz), 7.82 (1H, s).

MS (FAB): m/z 218 (M+H)$^+$.

c) An aqueous solution (60 ml) of sodium hydroxide (5.6 g, 140 mmol) was cooled to –50° C., to which bromine (2.67 ml, 51.7 mmol) was added dropwise. Then a solution of 2-acetamide-5-acetylindan (2.1 g, 9.8 mmol) in dioxane (70 ml) was added and stirred at room temperature for 3 hours. The reaction mixture was cooled in ice water, and sodium hydrogen sulfite was added thereto to decompose an excess of bromine. After the reaction mixture was washed with ether, it was acidified by adding concentrated hydrochloric acid, which was then extracted with methylene chloride. The organic layer was allowed to stand, and the precipitate that deposited was filtered to obtain 2-acetamide-5-carboxyindan (2.0 g, 8.9 mmol) having the following physical properties:

$^1$H NMR (400 MHz, DMSO-d$_6$); δ1.77 (3H, s), 2.77–2.82 (2H, m), 3.17–3.23 (2H, m), 4.76 (1H, m), 7.32 (1H, d, J=8.7 Hz), 7.75 (1H, d, J=8.7 Hz), 7.78 (1H, s), 8.12 (1H, d, J=6.4 Hz), 12.70 (1H, broad).

MS (FAB): m/z 220 (M+H)$^+$.

d) 2-acetamide-5-carboxyindan (2.0 g, 8.9 mmol) was suspended in water (12 ml) and concentrated hydrochloric acid (12 ml), and the suspension was heated to reflux for 7 hours. After the reaction mixture was washed with ether, water was distilled off under reduced pressure to obtain 2-amino-5-carboxyindan hydrochloride (1.9 g, 8.8 mmol) having the following physical properties:

$^1$H NMR (400 MHz, DMSO-d$_6$): δ3.04 (2H, m), 3.33 (2H, m), 4.03 (1H, m), 7.39 (1H, m), 7.80 (1H, m), 7.84 (1H, m), 8.29 (3H, br.), 12.82 (1H, br.).

MS (FAB): m/z 178 (M+H)$^+$.

e) A mixture of 2-amino-5-carboxyindan hydrochloride (1.9 g, 8.7 mmol), an aqueous solution of 1N sodium hydroxide (17.4 ml), dioxane (38 ml), water (19 ml) and di-tert-butyldicarbonate (2.1 g, 9.6 mmol) was stirred at room temperature for 30 minutes. The reaction mixture was extracted with ethyl acetate, the organic layer was dried, and the solvent was distilled off under reduced pressure to obtain the title compound (1.8 g, 6.5 mmol).

Preparation Example 5

2-(tert-butoxycarbonylamino)-4-hydroxyindan a) Using 4-methoxy-1-indanone (1.0 g, 6.2 mmol) instead of 6-methoxy-1-indanone, methanol (20 ml), isoamyl nitrite (0.81 ml, 5.9 mmol) and concentrated hydrochloric acid (0.25 ml), a similar procedure to a) in Method 1 of Preparation Example 1 was carried out to obtain 4-methoxy-2-oxyimino-1-indanone (350 mg, 1.8 mmol) having the following physical properties:

$^1$H NMR (400 MHz, DMSO-d$_6$): δ3.60 (2H, s), 3.90 (3H, s), 7.33 (1H, m), 7.47 (1H, t, J=8 Hz), 7.69 (1H, d, J=8 Hz), 12.70 (1H, br. s).

MS (FAB): m/z 192 (M+H)$^+$.

b) 4-methoxy-2-oxyimino-1-indanone (400 mg, 2.1 mmol) was suspended in acetic acid (7.6 ml). Palladium carbon (5%, 200 mg) and concentrated sulfuric acid (0.50 ml) were added thereto, and the mixture was stirred under a hydrogen atmosphere at ordinary pressure for 1.5 hours. Then a similar procedure to b) in Method 1 of Preparation Example 1 was carried out to obtain 2-amino-4-methoxyindan (290 mg, 1.8 mmol).

$^1$H NMR (400 MHz, DMSO-d$_6$): δ2.45 (2H, m), 2.98 (2H, m), 3.68 (1H, m), 6.72 (1H, d, J=8 Hz), 6.77 (1H, d, J=8 Hz), 7.09 (1H, t, J=8 Hz)

MS (FAB): m/z 164 (M+H)$^+$.

IR (KBr): ν3450, 2940, 1590, 1480, 1260, 1070 cm$^{-1}$.

c) After 2-amino-4-methoxyindan (290 mg, 1.8 mmol) was demethylated using 30% hydrobromic acid-acetic acid (1.8 ml) and an aqueous solution of 48% hydrobromic acid (1.2 ml), a similar procedure to c) in Method 1 of Preparation Example 1 was carried out using dioxane (5.9 ml), water (3.0 ml), triethylamine (about 0.55 ml), and di-tert-butyldicarbonate (420 mg, 1.9 mmol) to obtain the title compound (110 mg, 0.45 mmol) having the following physical properties:

$^1$H NMR (400 MHz, DMSO-d$_6$): δ1.39 (1H, s), 2.59 (1H, m), 2.71 (1H, m), 3.04 (2H, m), 4.16 (1H, m), 6.56 (1H, d, J=8 Hz), 6.61 (1H, d, J=7 Hz), 6.93 (1H, t, J=8 Hz), 7.09 (1H, br. s), 9.09 (1H, s).

MS (FAB): m/z 250 (M+H)$^+$.

Preparation Example 6

2-tert-butoxycarbonylamino)-4-[(E)-2-(4-methylphenyl) ethenyl]indan a) Using 2-(tert-butoxycarbonylamino)-4-hydroxyindan (110 mg, 0.45 mmol) instead of 2-(tert-butoxycarbonylamino)-5-hydroxyindan, pyridine, (0.5 ml), and trifluoromethanesulfonic anhydride (91 μl, 0.54 mmol), a similar procedure to a) in Preparation Example 2 was carried out. The product was purified by silica gel chromatography (hexane:ethyl acetate=3:1) to obtain 2-(tert-butoxycarbonylamino)-4-trifluoromethanesulfonyloxyindan (130 mg, 0.35 mmol).

$^1$H NMR (400 MHz, CDCl$_3$): δ1.45 (9H, s), 2.90 (2H, m), 3.36 (2H, m), 4.52 (1H, br. s), 4.72 (1H, br. s), 7.08 (1H, d, J=7 Hz), 7.25 (2H, m).

MS (FAB): m/z 382 (M+H)$^+$.

b) Using 2-(tert-butoxycarbonylamino)-4-trifluoromethanesulfonyloxyindan (130 mg, 0.35 mmol), (E)-2-(4-methylphenyl)ethenylboronic acid (110 mg), toluene (3.4 ml), Pd(PPh$_3$)$_4$ (15 mg, 0.013 mmol), an aqueous solution of 2M sodium carbonate (0.5 ml), ethanol (1.6 ml) and lithium chloride (32 mg, 0.75 mmol), a similar procedure to c) in Preparation Example 2 was carried out. The product obtained was purified by silica gel chromatography (hexane:ethyl acetate=6:1) to obtain the title compound (70 mg, 0.20 mmol) having the following physical properties:

$^1$H NMR (400 MHz, CDCl$_3$): δ1.45 (9H, s), 2.36 (3H, s), 2.81 (1H, dd, J=5 Hz, 16 Hz), 2.93 (1H, m), 3.30 (1H, dd,

J=7 Hz, 16 Hz), 3.42 (1H, dd, J=7 Hz, 16 Hz), 4.50 (1H, br. s), 4.77 (1H, br. s), 7.05 (1H, d, J=12 Hz), 7.12 (1H, d, J=12 Hz), 7.18 (3H, m), 7.42 (3H, m).

MS (FAB): m/z 349 (M)+.

Preparation Example 7

2-(tert-butoxycarbonylamino)-4-methoxycarbonylindan

Using 2-(tert-butoxycarbonylamino)-4-[(E)-2-(4-methylphenyl)ethenyl]indan (70 mg, 0.20 mmol) synthesized in Preparation Example 6, osmium tetraoxide (on poly (4-vinylpyridine), 53 mg), sodium metaperiodate (170 mg, 0.79 mmol), dioxane (1.5 ml), and water (0.3 ml), a similar procedure to Preparation Example 3. was carried out to obtain an aldehyde mixture (73 mg).

Subsequently, using methanol (3 ml), sodium cyanide (120 mg, 2.4 mmol), acetic acid (44 µl), and manganese dioxide (800 mg, 9.4 mmol), the aldehyde mixture (73 mg) was treated in a similar procedure to Preparation Example 3. The product obtained was purified by silica gel chromatography (hexane:ethyl acetate=4:1) to obtain the title compound (45 mg, 0.15 mmol) having the following physical properties:

$^1$H NMR (400 MHz, CDCl$_3$): δ1.45 (9H, s), 2.84 (1H, m), 3.17 (1H, m), 3.30 (1H, m), 3.62 (1H, m), 4.47 (1H, br. s), 4.71 (1H, br. s), 7.24 (1H, m), 7.39 (1H, d, J=8 Hz), 7.85 (1H, d, J=8 Hz).

MS (FAB): m/z 292 (M+H)+, 236 (M+H−56)+.

Example 1

4-(2-indanylamino)-5-methylthieno[2,3-d]pyrimidine 4-chloro-5-methylthieno[2,3-d]pyrimidine (92 mg, 0.50 mmol) (see J. Pharm. Soc. JAPAN, 109, 464 (1989)) and 2-aminoindan (330 mg, 2.5 mmol) in dry ethanol (1 ml) were heated to reflux under an argon atmosphere for 40 minutes. The solvent was distilled off under reduced pressure and the residue obtained was purified by silica gel chromatography (hexane:ethyl acetate=5:1) to obtain the title compound (140 mg, 0.50 mmol) having the following physical properties:

$^1$H NMR (400 MHz, CDCl$_3$): δ2.47 (3H, s), 2.94 (2H, m), 3.50 (2H, m), 5.11 (1H, m), 5.65 (1H, br.), 6.80 (1H, s), 7.19–7.27 (4H, m), 8.47 (1H, s).

MS (FAB): m/z 282 (M+H)+.

Example 2

4-(2-indanylamino)thieno[3,4-d]pyrimidine 4-methylthiothieno[3,4-d]pyrimidine (90 mg, 0.50 mmol) (see J. Heterocyclic Chem., 30, 509 (1993)) and 2-aminoindan (200 mg, 1.5 mmol) in dry ethanol (4 ml) were heated to reflux under an argon atmosphere for 4 hours. The solvent was distilled off under reduced pressure and the residue obtained was purified by silica gel chromatography (ethyl acetate:methanol=20:1) to obtain the title compound (30 mg, 0.11 mmol) having the following physical properties;

$^1$H NMR (400 MHz, DMSO-d$_6$): δ3.02 (2H, m), 3.38 (2H, m), 4.99 (1H, m), 7.17 (2H, m), 7.27 (2H, m), 7.74 (1H, s), 8.17 (1H, s), 8.44 (1H, d, J=6 Hz), 8.52 (1H, s).

MS (FAB): m/z 268 (M+H)+.

Example 3

4-(2-indanylamino)-7-methylthieno[3,2-d]pyrimidine 4-chloro-7-methylthieno[3,2-d]pyrimidine (74 mg, 0.40 mmol) and 2-aminoindan (270 mg, 2.0 mmol) in dry ethanol (3 ml) were heated to reflux under an argon atmosphere for 1 hour. The solvent was distilled off under reduced pressure and the residue obtained was purified by silica gel chromatography (hexane:ethyl acetate=1:1) to obtain the title compound (83 mg, 0.30 mmol) having the following physical properties:

$^1$H NMR (400 MHz, DMSO-d$_6$): δ2.33 (3H, s), 3.03 (2H, m) 3.33 (2H, m), 4.98 (1H, m), 7.16 (2H, m), 7.24 (2H, m), 7.71 (1H, s), 7.98 (1H, d, J=7 Hz), 8.51 (1H, s).

MS (FAB): m/z 282 (M+H)+.

Example 4

4-(2-indanylamino)pyrrolo[2,3-d]pyrimidine 4-chloropyrrolo[2,3-d]pyrimidine (83 mg, 0.54 mmol) (see J. Chem. Soc., 131 (1960), J. Org. Chem., 26, 3809 (1961)) and 2-aminoindan (220 mg, 1.6 mmol) in dry ethanol (5 ml) were heated to reflux under an argon atmosphere for 1 hour. The solvent was distilled off under reduced pressure and the residue obtained was purified by silica gel chromatography (ethyl acetate) to obtain the title compound (38 mg, 0.20 mmol) having the following physical properties:

$^1$H NMR (400 MHz, DMSO-d$_6$): δ2.96 (2H, m), 3.32 (2H, m), 4.92 (1H, m), 6.57 (1H, m), 7.05 (1H, m), 7.16 (2H, m), 7.25 (2H, m), 7.51 (1H, d, J=8 Hz), 8.13 (1H, s), 11.4 (1H, br.).

MS (FAB): m/z 251 (M+H)+.

Example 5

4-(2-indanylamino)thieno[2,3-d]pyrimidine a) To acetic anhydride (4.7 ml) under ice cooling, formic acid (4.7 ml) was added dropwise, to which 2-aminothiophene-3-carboxylic acid ethyl ester (2.8 g, 16.4 mmol) was added and stirred at room temperature for 2 hours. After the solvent was distilled off under reduced pressure, ether was added, and the precipitate that deposited was filtered off. Ether was distilled off under reduced pressure to obtain 2-formylaminothiophene-3-carboxylic acid ethyl ester (3.0 g, 15.3 mmol).

b) 2-formylaminothiophene-3-carboxylic acid ethyl ester (3.0 g, 15.3 mmol) was dissolved in formamide (12 ml), to which ammonium formate (3.0 g, 48.2 mmol) was added and the mixture was stirred at 150° C. for 6 hours. The reaction mixture was allowed to stand overnight at room temperature and the crystals that formed were filtered to obtain 4-hydroxythieno[2,3-d]pyrimidine (1.7 q, 11.0 mmol) having the following physical properties:

$^1$H NMR (400 MHz, DMSO-d$_6$): δ7.39 (1H, d, J=5.8 Hz), 7.58 (1H, d, J=5.8 Hz), 8.11 (1H, s), 12.45 (1H, broad).

MS (FAB): m/z 153 (M+H)+.

c) 4-hydroxythieno[2,3-d]pyrimidine (300 mg, 2.0 mmol) in phosphorous oxychloride (1.5 ml) was heated to reflux for 1 hour. 4-chlorothieno[2,3-d]pyrimidine obtained by distilling off the solvent under reduced pressure. Without further purification of 4-chlorothieno[2,3-d]pyrinidine the resultant mixture was heated to reflux with 2-aminoindane (1.1 g, 8.0 mmol) in dry ethanol (6 ml) under an argon atmosphere for 2 hours. The residue obtained by distilling off the solvent was purified by silica gel chromatography (hexane:ethyl acetate=5:2) to obtain the title compound (150 mg, 0.56 mmol) having the following physical properties:

¹H NMR (400 MHz, CDCl₃): δ2.98 (2H, m), 3.50 (2H, m), 5.15 (1H, m), 5.33 (1H, br.), 7.08 (1H, d, J=6 Hz), 7.21–7.29 (5H, m), 8.54 (1H, s).

MS (FAB): m/z 268 (M+H)⁺.

Example 6

4-(2-indanylamino)furo[2,3-d]pyrimidine a) Malononitrile (0.50 g, 7.6 mmol), glycol aldehyde (0.32 g, 2.7 mmol), and triethylamine (0.40 ml, 2.9 mmol) were suspended in toluene (8.7 ml) and the mixture was heated to reflux for 10 minutes. The reaction mixture was washed with brine, dried over anhydrous magnesium sulfate, and then the solvent was distilled off under reduced pressure to obtain 2-amino-3-cyanofuran (0.27 g, 2.5 mmol).

b) A mixture of 2-amino-3-cyanofuran (270 mg, 2.5 mmol), triethyl orthoformate (1.5 ml, 9.0 mmol), and acetic anhydride (0.18 ml, 1.9 μmol) was heated to reflux at 130° C. for 2 hours. The reaction mixture was cooled, and 2-aminoindan (670 mg, 5.0 mmol), sodium acetate (640 mg, 7.8 mmol), and acetic acid (1.1 ml, 19 mmol) were added, which was further heated to reflux at 130° C. for 2 hours. The residue obtained by distilling off the solvent under reduced pressure was purified by silica gel chromatography (hexane:ethyl acetate=2:1) to obtain the title compound (44 mg, 0.18 mmol) having the following physical properties:

¹H NMR (400 MHz, CDCl₃); δ2.98 (2H, m), 3.47 (2H, m), 5.05 (1H, m), 5.37 (1H, br.), 6.63 (1H, s), 7.20–7.30 (4H, m), 7.47 (1H, s), 8.44 (1H, s).

MS (FAB): m/z 252 (M+R)⁺.

IR (KBr): v3490, 3250, 1620, 1590, 1510, 1480, 1140 cm⁻¹.

Example 7

4-(2-indanylamino)pyrazolo[3,4-d]pyrimidine

Using 4-hydroxypyrazolo[3,4-d]pyrimidine (140 mg, 1.0 mmol), phosphorus oxichloride (3.0 ml), and dimethylaniline (0.39 ml, 3.1 μmol), and then 2-aminoindan (400 mg, 3.0 mmol), a similar procedure to Preparation Example 5 was carried out. The product obtained was purified by silica gel chromatography (hexane:ethyl acetate=5:2) to obtain the title compound (150 mg, 0.56 mmol) having the following physical properties:

¹H NMR (400 MHz, DMSO-d₆): δ2.95 (2H, m), 3.34 (2H, m), 4.94 (1H, m), 7.17 (2H, m), 7.27 (2H, m), 8.12 (1H, s), 8.26 (1H, s), 8.33 (1H, br.).

MS (FAB): m/z 252 (M+H)⁺.

Example 8

7-(2-indanylamino) -υ-triazolo[4,5-d]pyrimidine 4,5-diamino-6-chloropyrimidine (140 mg, 0.97 mmol) (see J. Am. Chem. Soc., 76, 6073 (1954)) and isoamyl nitrite (0.15 ml, 1.1 mmol) in dry dioxane (7 ml). were heated to reflux for 1.5 hours. The reaction mixture was cooled and 2-aminoindan (280 mg, 2.1 mmol) was added thereto, and the mixture was further heated to reflux for 1 hour. The reaction mixture was allowed to stand overnight at room temperature and the precipitate that deposited was filtered off. The residue obtained after concentrating the filtrate under reduced pressure was purified by silica gel chromatography (methylene chloride:methanol=20:1). The product obtained was crystallized from ethanol to obtain the title compound (100 mg, 0.40 mmol) having the following physical properties:

mp: 229–231° C.

¹H NMR (400 MHz, DMSO-d₆): δ3.09 (2H, m), 3.25 (2H, m), 5.02 (1H, m), 7.17 (2H, m), 7.24 (2H, m), 8.39 (1H, s), 9.07 (1H, br.), 15.94 (1H, br.).

MS (FAB): m/z 253 (M+H)⁺.

Example 9

7-(2-indanylamino)oxazolo[5,4-d]pyrimidine 4-cyano-5-ethoxymethyleneaminooxazole (240 mg, 1.5 mmol) (see J. Am. Chem. Soc., 88, 3829 (1966), Bull. Chem. Soc. JAPAN, 43, 187 (1970), Bull. Chem. Soc. JAPAN, 43, 3909 (1970)) and 2-aminoindan (580 mg, 4.4 mmol) in dry ethanol (2 ml) were heated to reflux for 6.5 hours. The residue obtained by distilling off the solvent under reduced pressure was purified by silica gel chromatography (methylene chloride:ethyl acetate=1:4) to obtain the title compound (56 mg, 0.22 mmol) having the following physical properties:

¹H NMR (400 MHz, DMSO-d₆): δ3.12 (2H, m), 3.30 (2H, m), 4.97 (1H, br.), 7.16 (2H, m), 7.23 (2H, m), 8.37 (1H, br.), 8.51 (1H, br.), 8.62 (1H, s).

MS (FAB): m/z 253 (M+H)⁺.

Example 10

3-methyl-4-(2-indanylamino)isoxazolo[5,4-d] pyrimidine 4-cyano-5-ethoxymethyleneamino-3-aminoisoxazole (320 mg, 1.8 mmol) (see J. Org. Chem., 29, 2116 (1964)) and 2-aminoindan (710 mg, 5.3 mmol) in dry ethanol (3 ml) were heated to reflux for 1.5 hours. The residue obtained by distilling off the solvent under reduced pressure was purified by silica gel chromatography (hexane:ethyl acetate=2:1). The product obtained was crystallized from ethanol to obtain the title compound (270 mg, 0.38 mmol) having the following physical properties:

mp: 208° C.

¹H NMR (400 MHz, DMSO-d₆): δ2.62 (3H, s), 3.11 (2H, m), 3.35 (2H, m), 5.12 (1H, m), 7.17 (2H, m), 7.24 (2H, m), 7.60 (1H, br.), 8.46 (1H, s).

MS (FAB): m/z 267 (M+H)⁺.

IR (KBr): v3260, 1590, 1500, 1460, 1320, 1250, 1220 cm⁻¹.

Example 11

7-(2-indanylamino)thiazolo[5,4-d]pyrimidiue

Using 7-chlorothiazolo[5,4-d]pyrimidine (50 mg, 0.29 mmol) (see J. Org. Chem., 26, 4961 (1961), Chem. Pharm. Bull., 16, 750 (1968)) and 2-aminoindan (120 mg, 0.90 mmol), a similar procedure to Example 1 was carried out. The product obtained was purified by silica gel chromatography (hexane:ethyl acetate=2:1) to obtain the title compound (41 mg, 0.15 mmol) having the following physical properties:

¹H NMR (400 MHz, CDCl₃): δ3.01 (2H, m), 3.50 (2H, m), 5.14 (1H, br.), 6.33 (1H, br.), 7.19–7.28 (4H, m), 8.56 (1H, s), 8.74 (1H, s), 8.49 (1H, s).

MS (FAB): m/z 269 (M+H)⁺.

Example 12

2-(2-indanylamino)-1-thia-2,3,5,7-tetraazaindene

Using 2-chloro-1-thia-2,3,5,7-tetraazaindene (50 mg, 0.29 mmol) (see J. Org. Chem. 26, 4961 (1961), J. Chem.

Soc. (C) 1856 (1967)) and 2-aminoindan (120 mg, 0.90 mmol), a similar procedure to Example 1 was carried out. The product obtained was purified by silica gel chromatography (hexane:ethyl acetate=3:1) to obtain the title compound (41 mg, 0.15 mmol) having the following physical properties:

$^1$H NMR (400 MHz, CDCl$_3$): δ3.08 (2H, m), 3.53.(2H, m), 5.25 (1H br.), 6.99 (1H, br.), 7.22–7.30 (4H, m), 8.66 (1H, s).

MS (FAB): m/z 270 (M+H)$^+$.

Example 13

6-(2-indanylamino)-7-methylisothiazolo[3,4-d]pyrimidine

A mixture of 3-amino-5-methyl-4-isothiazole carbonitrile (270 mg, 1.9 mmol) (see Arch. Pharm. Ber. Dtsch. Pharm. Ges., 301, 611 (1968), Angew. Chem. internat. Edit., 6, 83 (1967)), triethyl orthoformate (1.9 ml, 12 mmol), and acetic anhydride (1.9 ml, 20 mol) was heated to reflux at 130° C. for 2 hours. After the reaction mixture was concentrated under reduced pressure, dry ethanol (3 ml) and 2-aminoindan (780 mg, 5.8 mmol) were added, and was further heated to reflux for 1 hour. The residue obtained by distilling off the solvent under reduced pressure was purified by silica gel chromatography (methylene chloride:ethyl acetate=1:3) to obtain the title compound (100 mg, 0.35 mmol) having the following physical properties:

$^1$H NMR (400 MHz, DMSO-d$_6$): δ3.04 (3H, s), 3.14 (2H, m), 3.39 (2H, m), 5.12 (1H, m), 7.18 (2H, m), 7.25 (2H, m), 7.32 (1H, br.), 8.35 (1H, s).

MS (FAB): m/z 283 (M+H)$^+$.

Example 14

7-(2-indanylamino)-1,3-dimethyl-1H-pyrazolo[4,3-d]pyrimidine 7-chloro-1,3-dimethyl-1H-pyrazolo[4,3-d]pyrimidine (28 mg, 0.15 mmol) (see J. Med. Chem.,31, 454 (1988)), 2-aminoindan (66 mg, 0.50 mmol), and triethylamine (30 μl, 0.2 μmol) in dry methylene chloride (1 ml) were heated to reflux for 2 hours. The residue obtained by distilling off the solvent under reduced pressure was purified by silica gel chromatography (hexane:ethyl acetate=1:4) to obtain the title compound (26 mg, 0.093 mmol) having the following physical properties:

$^1$H NMR (400 MHz, DMSO-d$_6$): δ2.38 (3H, s), 3.09 (2H, m) 3.39 (2H, m), 4.14 (3H, s), 5.06 (1H, m), 7.17 (2H, m), 7.24 (2H, m), 8.26 (1H, s).

MS (FAB): m/z 280 (M+H)$^+$.

Example 15

4-(2-indanylamino)pyrido[2,3-d]pyrimidine

Using 4-hydroxypyrido[2,3-d]pyrimidine (150 mg, 1.0 mmol) (see J. Am. Chem. Soc., 77, 2256 (1955)), phosphorus oxychloride (1.0 ml), 2-aminoindan (270 mg, 2.0 mmol), triethylamine (1.4 ml, 10 mmol), and dry dioxane (5 ml), a similar procedure to Example 14 was carried out. The product obtained was purified by silica gel chromatography (ethyl acetate:methanol=19:1) to obtain the title compound (60 mg, 0.23 mmol) having the following physical properties:

$^1$H NMR (400 MHz, CDCl$_3$): δ3.06 (2H, m), 3.39 (2H, m), 5.05 (1H, m), 7.17 (2H, m), 7.26 (2H, m), 7.51 (1H, m), 8.60 (1H, br. d), 8.65 (1H, s), 8.80 (1H, m), 8.98 (1H, m).

MS (FAB): m/z 293 (M+H)$^+$.

Example 16

4-[N-(2-indanyl)-N-methylamino]-5-methylthieno[2,3-d]pyrimidine

A compound of the above Example 1, 4-(2-indanylamino)-5-methylthieno[2,3-d]pyrimidine (29 mg, 0.10 mmol), was dissolved in dry dimethylformamide (0.5 ml), to which sodium hydride (4.4 mg, 0.11 mmol) was added. After the mixture was stirred at room temperature for 10 minutes, methyl iodide (7.0 μl, 0.11 mmol) was added to the reaction mixture, which was further stirred at room temperature for 30 minutes. Water was added to the reaction mixture, which was extracted with chloroform, and the organic layer was dried over anhydrous sodium sulfate. The residue obtained by distilling off the solvent under reduced pressure was purified by silica gel chromatography (hexane:ethyl acetate=2:1) to obtain the title compound (20 mg, 0.070 mmol) having the following physical properties:

$^1$H NMR (400 MHz, CDCl$_3$): δ2.60 (3H, s), 2.87 (3H, s), 3.13 (2H, m), 3.31 (2H, m), 4.87 (1H, m), 6.98 (1H, s), 7.17 (2H, m), 7.23 (2H, m), 8.59 (1H, s).

MS (FAB): m/z 296 (M+H)$^+$.

Example 17

4-(2-indanylamino)-5-phenylthieno[2,3-d]pyrimidine

Using 4-chloro-5-phenylthieno[2,3-d]pyrimidine (50 mg, 0.20 mmol) and 2-aminoindan (110 mg, 0.80 mmol), a similar procedure to Example 1 was carried out. The product obtained was purified by silica gel chromatography (hexane:ethyl acetate=2:1) to obtain the title compound (67 mg, 0.20 mmol) having the following physical properties:

$^1$H NMR (400 MHz, CDCl$_3$): δ2.54 (2H, m), 3.27 (2H, m), 4.92 (1H, m), 5.18 (1H, br.), 7.03 (1H, s), 7.15 (4H, m), 7.21–7.35 (5H, m), 8.53 (1H, s).

MS (FAB): m/z 344 (M+H)$^+$.

Example 18

4-(2-indanylamino)-5-(2-thienyl)thieno[2,3-d]pyrimidine

Using 4-chloro-5-(2-thienyl)thieno[2,3-d]pyrimidine (50 mg, 0.20 mmol) and 2-aminoindan (110 mg, 0.80 mmol), a similar procedure to Example 1 was carried out. The product obtained was purified by silica gel chromatography (hexane:ethyl acetate=1:1) to obtain the title compound (70 mg, 0.20 mmol) having the following physical properties:

$^1$H NMR (400 MHz, CDCl$_3$): δ2.66 (2H, m), 3.34 (2H, m), 5.00 (1H, m), 5.77 (1H, br.), 6.85 (1H, m), 6.89 (1H, m), 7.18 (4H, m), 7.22 (1H, s), 7.29 (1H, m), 8.55 (1H, s).

MS (FAB): m/z 350 (M+H)$^+$.

Example 19

5-(2-furyl)-4-(2-indanylamino)thieno[2,3-d]pyrimidine a) Ethyl 2-amino-4-(2-furyl)thiophene-3-carboxylate (500 mg, 2.1 mmol) in formamide (4 ml) was stirred at 180° C. for 3 hours. The precipitate obtained by cooling the reaction mixture was filtered to obtain 5-(2-furyl)-4-hydroxythieno[2,3-d]pyrimidine (330 mg, 1.5 mmol) having the following physical properties:

¹H NMR (400 MHz, DMSO-d₆): δ6.56 (1H, m), 7.56 (1H, d, J=3 Hz), 7.72 (2H, m), 8.14 (1H, s), 12.52 (1H, br. d).

b) 5-(2-furyl)-4-hydroxythieno[2,3-d]pyrimidine (180 mg, 0.80 mmol) in phosphorus oxychloride (2.0 ml) was heated to reflux for 2 hours. 5-(2-furyl)-4-chlorothieno[2,3-d]pyrimidine obtained by distilling off the solvent under reduced pressure, without further purification, together with 2-aminoindan (130 mg, 0.98 mmol) and triethylamine (0.90 ml, 6.4 mmol) in dry ethanol (5 ml) was heated to reflux under an argon atmosphere for 2 hours. The residue obtained by distilling off the solvent was purified by silica gel chromatography (hexane:ethyl acetate=2:1) to obtain the title compound (130 mg, 0.39 mmol) having the following physical properties:

¹H NMR (400 MHz, CDCl₃): δ2.86 (2H, m), 3.43 (2H, m), 5.14 (1H, m), 6.40 (1H, m), 6.44 (1H, m), 6.79 (1H, br.), 7.09 (1H, m), 7.20–7.30 (4H, m), 8.53 (1H, s).

MS (FAB): m/z 334 (M+H)⁺.

Example 20

4-(2-indanylamino)-5,6-dimethylthieno[2,3-d]pyrimidine a) Using ethyl 2-amino-4,5-dimethylthiophene-3-carboxylate (500 mg, 2.5 mmol) and formamide (5 ml), a similar procedure to a) in Example 19 was carried out to obtain 4-hydroxy-5,6-dimethylthieno[2,3-d]pyrimidine (380 mg, 2.1 mmol) having the following physical properties:

¹H NMR (400 MHz, DMSO-d₆): δ2.35 (3H, s), 2.39 (3H, s), 7.98 (1H, s), 12.17 (1H, br. s).

b) Using 4-hydroxy-5,6-dimethylthieno[2,3-d]pyrimidine (180 mg, 1.0 mmol), phosphorus oxychloride (1.0 ml), 2-aminoindan (270 mg, 2.0 mmol), triethylamine (0.84 ml, 6.0 mmol) and dry ethanol (5 ml), a similar procedure to b) in Example 19 was carried out. The product obtained was purified by silica gel chromatography (hexane:ethyl acetate=2:1) to obtain the title compound (190 mg, 0.64 mmol) having the following physical properties:

¹H NMR (400 MHz, CDCl₃): δ2.32 (3H, s), 2.38 (3H, s), 2.93 (2H, m), 3.50 (2H, m), 5.09 (1H, m), 5.62 (1H, br. d), 7.20 (2H, m), 7.26 (2H, m), 8.42 (1H, s).

MS (FAB): m/z 296 (M+H)⁺.

Example 21

4-(2-indanylamino)-5-[6-(3-methylpyridyl)]thieno[2,3-d]pyrimidine a) Using ethyl 2-amino-5-[6-(3-methylpyridyl)]thiophene-3-carboxylate (520 mg, 2.0 mmol) and formamide (4 ml), a similar procedure to a) in Example 19 was carried out to obtain 4-hydroxy-5-[6-(3-methylpyridyl)]thieno[2,3-d]pyrimidine (330 mg, 1.4 mmol) having the following physical properties:

¹H NMR (400 MHz, DMSO-d₆): δ7.27(1H, d, J=8 Hz), 7.61 (1H, s), 7.82 (1H, d, J=8 Hz), 8.15 (1H, s), 8.59 (1H, s), 12.48 (1H, br. s).

b) Using 4-hydroxy-5-[6-(3-methylpyridyl)]thieno[2,3-d]pyrimidine (240 mg, 1.0 mmol), phosphorus oxychloride (3.0 ml), 2-aminoindan (270 mg, 2.0 mmol), triethylamine (2.8 ml, 20 mmol) and dry ethanol (6 ml), a similar procedure to b) in Example 19 was carried out. The product obtained was purified by silica gel chromatography (methylene chloride:ethyl acetate=1:1) to obtain the title compound (140 mg, 0.38 mmol) having the following physical properties:

¹H NMR (400 MHz, CDCl₃): δ2.57 (3H, s), 2.60 (2H, m), 3.29 (2H, m), 4.97 (2H, m), 6.85 (1H, d, J=8 Hz), 7.06 (1H, s), 7.15–7.20 (4H, m), 7.35 (1H, m), 8.52 (1H, m), 8.54 (1H, s).

MS (FAB): m/z 359 (M+H)⁺.

Example 22

4-(2-indanylamino)-5-isopropylthieno[2,3-d]pyrimidine a) Using ethyl 2-amino-4-isopropylthiophene-3-carboxylate (800 mg, 3.8 mmol) and formamide (5 ml), a similar procedure to a) in Example 19 was carried out to obtain 4-hydroxy-5-isopropylthieno[2,3-d]pyrimidine (330 mg, 1.7 mmol) having the following physical properties:

¹H NMR (400 MHz, DMSO-d₆): δ1.33 (6H, d, J=7 Hz), 3.75 (1H, m), 6.95 (1H, s), 8.00 (1H, s), 11.43 (1H, br. s).

b) using 4-hydroxy-5-isopropylthieno[2,3-d]pyrimidine (200 mg, 1.03 mmol), phosphorus oxychloride (1.0 ml), 2-aminoindan hydrochloride (200 mg, 1.2 mmol), triethylamine (1.0 ml, 7.2 mmol) and dry ethanol (5 ml), a similar procedure to b) in Example 19 was carried out. The product obtained was purified by silica gel chromatography (hexane:ethyl acetate=2:1) to obtain the title compound (190 mg, 0.64 mmol) having the following physical properties:

¹H NMR (400 MHz, CDCl₃): δ1.25 (6H, d, J=7 Hz), 2.96 (3H, m), 3.50 (2H, dd, J=7 Hz, 16 Hz), 5.16 (1H, m), 5.63 (1H, br. d), 6.87 (1H, s), 7.20 (2H, m), 7.26 (2H, m), 8.49 (1H, s).

MS (FAB): m/z 310 (M+H)⁺.

Example 23

4-(5-methoxyindan-2-yl)amino-5-methylthieno[2,3-d]pyrimidine

Using 2-amino-5-methoxyindan (90 mg) synthesized in b) in the above Preparation Example 1, 4-chloro-5-methylthieno[2,3-d]pyrimidine (90 mg, 0.50 mmol), triethylamine (0.23 ml, 1.7 mmol) and ethanol (1 ml), a similar procedure to b) in Example 19 was carried out. The product obtained was purified by silica gel chromatography (hexane:ethyl acetate=4:1) to obtain the title compound (20 mg, 0.064 mmol) having the following physical properties:

¹H NMR (400 MHz, CDCl₃): δ2.47 (3H, s), 2.88 (2H, m), 3.45 (2H, m), 3.80 (3H, s), 5.10 (1H, m), 5.13 (1H, br. d), 6.76 (1H, m), 6.80 (2H, m), 8.47 (1H, s).

MS (FAB): m/z 312 (M+H)⁺.

Example 24

4-(5-hydroxyindan-2-yl)amino-5-methylthieno[2,3-d]pyrimidine

To 2-(tert-butoxycarbonylamino)-5-hydroxyindan (130 mg, 0.50 mmol) synthesized in the above Preparation Example 1 was added 4N hydrochloric acid-dioxane (2.3 ml) and acetic acid (6.9 ml), and the mixture was stirred at room temperature for 10 minutes. By distilling off the solvent under reduced pressure, 2-amino-5-hydroxyindan hydrochloride was obtained as a crude product. This was dissolved in ethanol (3 ml). Using triethylamine (0.14 ml, 1.0 mmol), 4-chloro-5-methylthieno[2,3-d]pyrimidine (83 mg, 0.60 mmol), a similar procedure to b) in Example 19 was carried out. The product obtained was purified by silica gel chromatography (methylene chloride:ethyl acetate=2:1) to obtain the title compound (17 mg, 0.057 mmol) having the following physical properties:

$^1$H NMR (400 MHz, DMSO-d$_6$): δ2.56 (3H, s), 2.94 (2H, m), 3.22 (2H, m), 4.97 (1H, m), 6.55 (2H, m), 6.63 (1H, s), 7.00 (1H, d, J=8 Hz), 7.14 (1H, s), 8.35 (1H, s), 9.06 (1H, s).

MS (FAB): m/z 298 (M+H)$^+$.

IR (KBr): ν3470, 1580, 1500 cm$^{-1}$.

Example 25

4-(5-phenoxyindan-2-yl)amino-5-methylthieno[2,3-d]pyrimidine a) 2-(tert-butoxycarbonylamino)-5-hydroxyindan (100 mg, 0.40 mmol) synthesized in the above Preparation Example 1 was dissolved in acetone (2 ml), to which potassium carbonate (58 mg, 0.45 mmol) and benzylbromide (48 μl, 0.40 mmol) were added, and the mixture was heated to reflux for 3 hours. The reaction mixture was extracted with ether and dried, and then the solvent was distilled off under reduced pressure to obtain 2-(tert-butoxycarbonylamino)-5-phenoxyindan (120 mg, 0.36 mmol) having the following physical properties:

$^1$H NMR (400 MHz, CDCl$_3$): δ1.44 (9H, s), 2.72 (2H, m), 3.22 (2H, m), 4.48 (1H, m), 4.74 (1H, m), 5.04 (2H, s), 6.79 (1H, m), 6.84 (1H, m), 7.09 (1H, m), 7.29–7.43 (5H, m)

MS (FAB): m/z 340 (M+H)$^+$.

b) Using 2-(tert-butoxycarbonylamino)-5-phenoxyindan (120 mg, 0.36 mmol), 4N hydrochloric acid-dioxane (1.7 ml) and acetic acid (5.1 ml), a similar procedure to Example 24 was carried out to obtain 2-amino-5-phenoxyindan hydrochloride (99 mg, 0.36 mmol) having the following physical properties:

$^1$H NMR (400 MHz, DMSO-d$_6$): δ2.88 (2H, m), 3.21 (2H, m), 3.98 (1H, m), 5.08 (1H, m), 6.84 (1H, m), 6.63 (1H, s), 6.95 (1H, m), 7.16 (1H, m), 7.32–7.43 (5H, m), 8.09 (2H, br.).

MS (FAB): m/z 240 (M+H)$^+$.

c) using 2-amino-5-phenoxyindan hydrochloride (99 mg, 0.36 mmol), ethanol (3 ml), triethylamine (92 μl, 0.66 mmol), and 4-chloro-5-methylthieno[2,3-d]pyrimidine (61 mg, 0.33 mmol), a similar procedure to b) in Example 19 was carried out. The product obtained was purified by silica gel chromatography (hexane:ethyl acetate=1:1) to obtain the title compound (51 mg, 0.13 mmol) having the following physical properties:

$^1$H NMR (400 MHz, CDCl$_3$): δ2.47 (3H, s), 2.87 (2H, m), 3.45 (2H, m), 5.05 (2H, s), 5.11 (1H, m), 5.63 (1H, br. d), 6.82 (2H, m), 6.89 (1H, s), 7.15 (1H, d, J=8 Hz), 7.32–7.44 (5H, m), 8.47 (1H, s).

MS (FAB): m/z 388 (M+H)$^+$.

IR (KBr): ν3460, 1570, 1500, 1450, 1240, 1010 cm$^{-1}$.

Example 26

4-[5-[(E)-2-(4-methylphenyl)ethenyl]indan-2-yl]amino-5-methylthieno[2,3-d]pyrimidine a) Using 2-(tert-butoxycarbonylamino)-5-[(E)-2-(4-methylphenyl)ethenyl]indan (20 mg, 0.060 mmol) synthesized in Preparation Example 2, 4N hydrochloric acid-dioxane (2.0 ml) and acetic acid (6.0 ml), a similar procedure to Example 24 was carried out to obtain 2-amino-5-[(E)-2-(4-methylphenyl)ethenyl]indan hydrochloride (16 mg, 0.06 mmol) having the following physical properties:

$^1$H NMR (400 MHz, MeOH-d$_4$): δ2.33 (3H, s), 3.02 (2H, m), 3.40 (2H, m), 4.10 (1H, m), 7.10–7.17 (4H, m), 7.27 (1H, m), 7.42 (3H, m), 7.49 (1H, m).

b) Using 2-amino-5-[(E)-2-(4-methylphenyl)ethenyl]indan hydrochloride (16 mg, 0.06 mmol), ethanol (0.6 ml), triethylamine (50 μl, 0.36 mmol), and 4-chloro-5-methylthieno[2,3-d]pyrimidine (11 mg, 0.060 mmol), a similar procedure to b) in Example 19 was carried out. The product obtained was purified by silica gel chromatography (hexane:ethyl acetate=4:1) to obtain the title compound (14 mg, 0.035 mmol) having the following physical properties:

$^1$H NMR (400 MHz, CDCl$_3$): δ2.36 (3H, s), 2.47 (3H, s), 2.93 (2H, m), 3.51 (2H, m), 5.13 (1H, m), 5.63 (1H, br. d), 6.80 (1H, s), 7.06 (2H, s), 7.16 (2H, m), 7.23 (1H, m), 7.34 (1H, m), 7.41 (3H, m), 8.48 (1H, s).

MS (FAB): m/z 398 (M+H)$^+$.

IR (KBr): ν1570, 1500 cm$^{-1}$.

Example 27

4-(5-methoxycarbonylindan-2-yl)amino-5-methylthieno[2,3-d]pyrimidine

Using 2-(tert-butoxycarbonylamino)-5-methoxycarbonylindan (60 mg, 0.21 mmol) synthesized in the above Preparation Example 3, 4N hydrochloric acid-dioxane (1.0 ml) and acetic acid (3.0 ml), and then ethanol (1 ml), triethylamine (88 μl, 0.63 mmol), and 4-chloro-5-methylthieno[2,3-d]pyrimidine (39 mg, 0.21 mmol), a similar procedure to Example 24 was carried out. The product obtained was purified by silica gel chromatography (methylene chloride:ethyl acetate=6:1) to obtain the title compound (32 mg, 0.094 mmol) having the following physical properties:

$^1$H NMR (400 MHz, CDCl$_3$): δ2.47 (3H, s), 2.98 (2H, m), 3.54 (2H, m), 3.91 (3H, s), 5.15 (1H, m), 5.60 (1H, br. d), 6.82 (1H, s), 7.32 (2H, m), 7.91 (1H, m), 7.94 (1H, m), 8.48 (1H, s).

MS (FAB): m/z 340 (M+H)$^+$.

IR (KBr): ν1720, 1570, 1500, 1270 cm$^{-1}$.

Example 28

4-(5-carboxyindan-2-yl)amino-5-methylthieno[2,3-d]pyrimidine sodium salt 4-(5-methoxycarbonylindan-2-yl)amino-5-methylthieno[2,3-d]pyrimidine (27 mg, 0.08 mmol) synthesized in the above Example 27, methanol (1 ml), and an aqueous solution of 1N sodium hydroxide (88 μl) were heated to reflux for 7 hours. To the residue obtained by distilling off the solvent under reduced pressure, ethyl acetate was added, and the precipitate that formed was filtered to obtain the title compound (25 mg, 0.072 mmol) having the following physical properties:

$^1$H NMR (400 MHz, DMSO-d$_6$): δ2.57 (3H, s), 3.03 (2H, m), 3.34 (2H, m), 5.01 (1H, m), 6.58 (1H, br. d), 7.08 (1H, m), 7.15 (1H, s), 7.68 (1H, m), 7.71 (1H, m), 8.37 (1H, s).

MS (FAB): m/z 326 (M+H)$^+$, 348 (M+Na)$^+$.

IR (KBr): ν3450, 1570, 1550, 1500, 1430, 1400 cm[<s]up−1.

Example 29

N-propyl-2-(5-methylthieno[2,3-d]pyrimidine-4-yl)amino-5-indan carboxamide a) 2-(tert-butoxycarbonylamino)-5-carboxyindan (30 mg, 0.11 mmol) synthesized in Preparation Example 4, n-propylamine (20 μl, 0.24 mmol), triethylamine (0.20 ml, 1.4 mmol), propanephosphonic acid anhydride (0;3 ml) (see Japanese Unexamined Patent Publication (Kokai) No. 55-100346), and dimethylaminopyridine (a catalytic amount) in methylene chloride (0.25 ml) were stirred at room temperature for 30 minutes. The reaction mixture was diluted with ethyl acetate, and then washed with, in the order of, an aqueous solution of saturated potassium hydrogen sulfate, brine, an aqueous solution of saturated sodium hydrogen carbonate, and brine, and then was dried over anhydrous sodium sulfate. The residue obtained by distilling off the solvent under reduced pressure was purified by silica gel chromatography (hexane:ethyl acetate=4:1 to 3:7) to obtain N-propyl-2-(tert-butoxycarbonylamino)-5-indan carboxamide (22 mg, 0.070 mmol) having the following physical properties:

$^1$H NMR (400 MHz, CDCl$_3$): δ0.99 (3H, t, J=8 Hz), 1.45 (9H, s), 1.65 (2H, q, J=7 Hz), 2.81 (2H, dd, J=5 Hz, 16 Hz), 3.31 (2H, dd, J=7 Hz, 16 Hz), 3.41 (2H, q, J=6 Hz), 4.50 (1H, br. s), 4.70 (1H, br. s), 6.07 (1H, br. s), 7.24 (1H, d, J=8 Hz), 7.55 (1H, d, J=8 Hz), 7.62 (1H, s).

MS (FAB): m/z 319 (M+H)$^+$.

IR (KBr): ν1690, 1640, 1540, 1170 cm$^{-1}$.

b) Using N-propyl-2-(tert-butoxycarbonylamino)-5-indan carboxamide (22 mg, 0.070 mmol), 4N hydrochloric acid-dioxane (2 ml) and acetic acid (6.0 ml), a similar procedure to Example 24 was carried out to obtain N-propyl-2-amino-5-indan carboxamide hydrochloride. Then using ethanol (1 ml), triethylamine (0.50 ml, 3.6 mmol), and 4-chloro-5-methylthieno[2,3-d]pyrimidine (18 mg, 1.0 mmol), a similar procedure to b) in Example 19 was carried out. The product obtained was purified by silica gel chromatography (hexane:ethyl acetate=2:1 to 1:2) to obtain the title compound (12 mg, 0.033 mmol) having the following physical properties:

$^1$H NMR (400 MHz, CDCl$_3$): δ0.99 (3H, t, J=7 Hz), 1.70 (2H, m), 2.46 (3H, d, J=1 Hz), 2.97 (2H, dd, J=5 Hz, 16 Hz), 3.42 (2H, q, J=6 Hz), 3.52 (2H, dd, J=7 Hz, 16 Hz), 5.12 (1H, m), 5.60 (1H, br. d), 6.10 (1H, br. s), 6.84 (1H, S), 7.29 (1H, d, J=8 Hz), 7.58 (1H, d, J=8 Hz), 7.68 (1H, s), 8.47 (1H, s).

MS (FAB): m/z 367 (M+H)$^+$.

IR (KBr): ν1650, 1570, 1490 cm$^{-1}$.

Example 30

N-phenyl-2-(5-methylthieno[2,3-d]pyrimidine-4-yl) amino-5-indan carboxamide a) Using 2-(tert-butoxycarbonylamino)-5-carboxyindan (30 mg, 0.11 mmol) synthesized in Preparation Example 4, aniline (21 μl, 0.23 mmol), triethylamine (0.20 ml, 1.4 mmol), propanephosphonic acid anhydride (0.3 ml), dimethylaminopyridine (a catalytic amount) and methylene chloride (0.25 ml), a similar procedure to a) in Example 29 was carried out. The product obtained was purified by silica gel chromatography (hexane:ethyl acetate=4:1 to 7:3) to obtain N-phenyl-2-(tert-butoxycarbonylamino)-5-indan carboxamide (27 mg, 0.077 mmol) having the following physical properties:

$^1$H NMR (400 MHz, CDCl$_3$): δ1.46 (9H, s), 2.85 (2H, dd, J=5 Hz, 16 Hz), 3.31 (2H, dd, J=7 Hz, 16 Hz), 4.40 (1H, m), 4.50 (1H, br. s), 4.75 (1H, br. s), 7.14 (1H, t, J=7 Hz), 7.35 (2H, d, J=8 Hz), 7.63 (2H, d, J=8 Hz), 7.66 (1H, d, J=8 Hz), 7.72 (1H, s), 7.81 (1H, s) .

MS (FAB): m/z 353 (M+H)$^+$.

IR (XBr): ν1680, 1540, 1170 cm$^{-1}$.

b) Using N-phenyl-2-(tert-butoxycarbonylamino)-5-indan carboxamide (27 mg, 0.077 mmol), 4N hydrochloric acid-dioxane (2.0 ml) and acetic acid (6.0 ml), a similar procedure to Example 24 was carried out to obtain N-phenyl-2-amino-5-indan carboxamide hydrochloride. Then using ethanol (1 ml), triethylamine (0.50 ml, 3.6 mmol), 4-chloro-5-methylthieno[2,3-d]pyrimidine (18 mg, 1.0 mmol), a similar procedure to b) in Example 19 was carried out. The product obtained was purified by silica gel chromatography (haxane:ethyl acetate=4:1 to 1:1) to obtain the title compound (8 mg, 0.020 mmol) having the following physical properties:

$^1$H NMR (400 MHz, CDCl$_3$-MeOH-d$_4$): δ2.50 (3H, s), 3.03 (2H, br. d, J=6 Hz), 3.57 (2H, dd, J=7 Hz, 16 Hz), 5.10 (1H, br. s), 6.87 (1H, s), 7.15 (1H, t, J=7 Hz), 7.66 (2H, d, J=8 Hz), 7.75 (1H, d, J=8 Hz), 7.82 (1H, s), 8.43 (1H, s).

MS (FAB): m/z 401 (M+H)$^+$.

IR (KBr): ν1640, 1560, 1500, 1370 cm$^{-1}$.

Example 31

N-benzyl-2-(5-methylthieno[2,3-d]pyrimidine-4-yl) amino-5-indan carboxamide a) Using 2-(tert-butoxycarbonylamino)-5-carboxyindan (400 mg, 1.44 mmol), benzylamine (0.24 ml, 2.2 mmol), triethylamine (1.4 ml, 10 mmol), propanephosphonic acid anhydride (2.1 ml), dimethylaminopyridine (a catalytic amount) and methylene chloride (12 ml), a similar procedure to a) in Example 29 was carried out. The product obtained was purified by silica gel chromatography (methylene chloride:methanol=95:5) to obtain N-benzyl-2-(tert-butoxycarbonylamino)-5-indan carboxamide (460 mg, 1.25 mmol) having the following physical properties:

$^1$H NMR (400 MHz, CDCl$_3$): δ1.44 (9H, s), 2.80 (2H, dd, J=4 Hz, 16 Hz), 3.27 (2H, dd, J=3 Hz, 12 Hz), 4.50 (1H, br. s), 4.64 (2H, d, J=5 Hz), 4.70 (1H, br. s), 6.34 (1H, br. s), 7.30 (6H, m), 7.59 (1H, d, J=8 Hz), 7.65 (1H, s).

IR (KBr): ν3300, 1690, 1640, 1540, 1280, 1170 cm$^{-1}$.

b) Using N-benzyl-2-(tert-butoxycarbonylamino)-5-indan carboxamide (820 mg, 2.2 mmol), 4N hydrochloric acid-dioxane (10 ml) and acetic acid (30 ml), a similar procedure to Example 24 was carried out to obtain N-benzyl-2-amino-5-indan carboxamide hydrochloride (660 mg, 2.2 mmol) having the following physical properties:

$^1$H NMR (400 MHz, DMSO-d$_6$): δ3.01 (2H, dd, J=5 Hz, 17 Hz), 3.32 (2H, dd, J=8 Hz, 17 Hz), 4.03 (1H, m), 4.48 (2H, d, J=6 Hz), 7.23–7.32 (5H, m), 7.36 (1H, d, J=8 Hz), 7.76 (1H, d, J=8 Hz), 7.81 (1H, s), 8.17 (3H, br), 8.96 (1H, m).

c) Using N-benzyl-2-amino-5-indan carboxamide hydrochloride (660 mg, 2.2 mmol), ethanol (19 ml), triethylamine (0.94 ml, 6.7 mmol), and 4-chloro-5-methylthieno[2,3-d] pyrimidine (410 mg, 2.2 mmol), a similar procedure to b) in Example 19 was carried out. A solid obtained by purifying the product by silica gel chromatography (methylene chloride:ethanol=95:5) was washed with ether to obtain the title compound (580 mg, 1.4 mmol) having the following physical properties:

$^1$H NMR (400 MHz, DMSO-d$_6$): δ2.57 (3H, s), 3.11 (2H, dd, J=7 Hz, 16 Hz), 3.42 (2H, dd, J=8 Hz, 10 Hz), 4.47 (2H, d, J=6 Hz), 5.05 (1H, m), 6.62 (1H, d, J=7 Hz), 7.15 (1H, s), 7.23 (1H, m), 7.31 (4H, m), 7.72 (1H, d, J=8 Hz), 7.78 (1H, s), 8.37 (1H, s), 8.92 (1H, m).

MS (FAB): m/z 415 (M+H)$^+$.

IR (XBr): ν1650, 1570, 1500 cm$^{-1}$.

Example 32

2-[5-methylthieno[2,3-d]pyrimidine-4-yl] aminoindan-5-carboxylic acid morpholinamide a) Using 2-(tert-butoxycarbonylamino)-5-carboxyindan (1.01 g, 3.6 mmol), morpholine (0.48 ml, 5.5 mmol), triethylamine (3.6 ml, 26 mmol), propanephosphonic acid anhydride (5.3 ml), dimethylaminopyridine (a catalytic amount) and methylene chloride (27 ml), a similar procedure to a) in Example 29 was carried out. The product obtained was purified by silica gel chromatography (methylene chloride:methanol=95:5) to obtain 2-(tert-butoxycarbonylamino)indan-5-carboxylic acid morpholinamide (1.0 g, 2.9 mmol) having the following physical properties:

$^1$H NMR (400 MHz, CDCl$_3$): δ1.45 (9H, s), 2.79 (2H, dd, J=3 Hz, 16 Hz), 3.27 (2H, dd, J=7 Hz, 16 Hz), 3.70 (8H, br. s), 4.40 (1H, br. s), 4.70 (1H, br. s), 7.25 (3H, m).

IR (KBr): ν3320, 2970, 1710, 1620, 1520, 1430, 1270, 1170, 1110 cm$^{-1}$.

b) Using 2-(tert-butoxycarbonylamino)indan-5-carboxylic acid morpholinamide (1.0 g, 2.7 mmol), 4N hydrochloric acid-dioxane (12 ml) and acetic acid (36 ml), a similar procedure to Example 24 was carried out to obtain 2-aminoindan-5-carboxylic acid morpholinamide hydrochloride (750 mg, 2.7 mmol) having the following physical properties:

$^1$H NMR (400 MHz, DMSO-d$_6$): δ2.99 (2H, m), 3.29 (2H, m), 3.59 (8H, br. s), 4.02 (1H, m), 7.24 (1H, d, J=8 Hz), 7.33 (3H, m), 8.20 (3H, br. s).

c) Using 2-aminoindan-5-carboxylic acid morpholinamide hydrochloride (750 mg, 2.7 mmol), ethanol (23 ml), triethylamine (1.1 ml, 8.2 mmol), and 4-chloro-5-methylthieno[2,3-d]pyrimidine (500 mg, 2.7 mmol), a similar procedure to b) in Example 19 was carried out. The product obtained was purified by silica gel chromatography (methylene chloride:methanol=95:5) to yield a fraction, which was then washed with ether to obtain the title compound (680 mg, 1.7 mmol) having the following physical properties:

$^1$H NMR (400 MHz, CDCl$_3$): δ2.49 (3H, s), 2.96 (2H, dd, J=5 Hz, 16 Hz), 3.54 (2H, dd, J=7 Hz, 16 Hz), 3.70 (8H, br. s), 5.10 (1H, m), 5.60 (1H, d, J=6 Hz), 7.25 (3H, m), 8.41 (1H, s).

MS (FAB); m/z 395 (M+H)$^+$.

IR (KBr): ν1570, 1500, 1110 cm$^{-1}$.

Example 33

4-(4-methoxyindan-2-yl)amino-5-methylthieno[2,3-d]pyrimidine

Using 2-amino-4-methoxyindan (27 mg, 0.17 mmol) synthesized in the above b) in Preparation Example 5, 4-chloro-5-methylthieno[2,3-d]pyrimidine (31 mg, 0.17 mmol), triethylamine (71 μl, 0.51 mmol), and ethanol (1.5 ml), a similar procedure to b) in Example 19 was carried out. The product obtained was purified by silica gel chromatography (hexane:ethyl acetate=2:1) to obtain the title compound (50 mg, 0.16 mmol) having the following physical properties:

$^1$H NMR (400 MHz, CDCl$_3$): δ2.48 (3H, s), 2.91 (2H, m), 3.49 (2H, m), 5.10 (1H, m), 5.63 (1H, br. d), 6.72 (1H, d, J=8 Hz), 6.80 (1H, rm), 6.87 (1H, d, J=7 Hz), 7.19 (1H, t, J=8 Hz), 8.47 (1H, s).

MS (FAB): m/z 312 (M+H)$^+$.

IR (KBr): ν3470, 1570, 1490, 1260, 1070 cm$^{-1}$.

Example 34

4-(4-methoxycarbonylindan-2-yl)amino-5-methylthieno[2,3-d]pyrimidine

Using 2-(tert-butoxycarbonylamino)-4-methoxycarbonylindan (45 mg, 0.15 mmol) synthesized in the above Preparation Example 7, 4N hydrochloric acid-dioxane (0.7 ml) and acetic acid (2.1 ml), a similar procedure to Example 24 was carried out to obtain 2-amino-4-methoxycarbonylindan hydrochloride. Then, using the 2-amino-4-methoxycarbonylindan hydrochloride, 4-chloro-5-methylthieno[2,3-d]pyrimidine (28 mg, 0.15 mmol), triethylamine (63 μl, 0.45 mmol), and ethanol (1 ml), a similar procedure to b) in Example 19 was carried out. The product obtained was purified by silica gel chromatography (hexane:ethyl acetate=2:1) to obtain the title compound (15 mg, 0.044 mmol) having the following physical properties:

$^1$H NMR (400 MHz, CDCl$_3$): δ2.49 (3H, s), 2.97 (1H, dd, J=5 Hz, 16 Hz), 3.33 (1H, dd, J=5 Hz, 18 Hz), 3.56 (1H, dd, J=7 Hz, 16 Hz), 3.86 (1H, dd, J=7 Hz, 18 Hz), 3.91 (3H, s), 5.11 (1H, m), 5.61 (1H, br. d), 6.81 (1H, s), 7.28 (1H, m), 7.44 (1H, d, J=8 Hz), 7.89 (1H, d, J=8 Hz), 8.48 (1H, s).

MS (FAB): m/z 340 (M+H)$^+$.

TR (KBr): ν3430, 1700, 1570, 1490, 1300 cm$^{-1}$.

Example 35

4-(5-acetoxyindan-2-yl)amino-5-methylthieno[2,3-d]pyrimidine a) 2-(tert-butoxycarbonylamino)-5-hydroxyindan (100 mg, 0.40 mmol) synthesized in Predagation Example 1 was dissolved in dry methylene chloride (2 ml), to which pyridine (0.19 ml, 2.3 mmol) and acetic anhydride (0.11 ml, 1.2 mmol) were added, and the mixture was stirred at room temperature for 2 hours. The reaction mixture then was concentrated under reduced pressure, to which diethylether was added. The organic layer was washed with, in the order of, an aqueous solution of saturated potassium hydrogen sulfate, brine, an aqueous solution of saturated sodium hydrogen carbonate, and brine, and then was dried over anhydrous sodium sulfate. The solvent was distilled off under reduced pressure to obtain 5-acetoxy-2-(tert-butoxycarbonylamino)indan (120 mg, 0.40 mmol) having the following physical properties:

$^1$H NMR (400 MHz, CDCl$_3$): δ1.45 (9H, s), 2.28 (3H, s), 2.77 (2H, m), 3.26 (2H, m), 4.47 (1H, m), 4.75 (1H, m), 6.86 (1H, d, J=8 Hz), 6.93 (1H, s), 7.19 (1H, d, J=8 Hz).

MS (FAB): m/z 292 (M+H)$^+$, 236 (M+H−56)$^+$.

b) Using 5-acetoxy-2-(tert-butoxycarbonylamino)indan (120 mg, 0.40 mmol), 4N hydrochloric acid-dioxane (2 ml) and acetic acid (6 ml), a similar procedure to Example 24 was carried out to obtain 5-acetoxy-2-aminoindan hydrochloride (86 mg, 0.38 mmol) having the following physical properties:

$^1$H NMR (400 MHz, DMSO-d$_6$): δ2.25 (3H, s), 2.95 (2H, m), 3.27 (2H, m), 4.02 (1H, m), 6.94 (1H, d, J=8 Hz), 7.03 (1H, s), 7.29 (1H, d, J=8 Hz), 8.17 (3H, br. S).

c) Using 5-acetoxy-2-aminoindan hydrochloride (86 mg, 0.38 mmol), 4-chloro-5-methylthieno[2,3-d]pyrimidine (76 mg, 0.41 mmol), triethylamine (0.23 ml, 1.6 mmol), and ethanol (6 ml), a similar procedure to b) in Example 19 was carried out. The product obtained was purified by silica gel chromatography (hexane:ethyl acetate=2:1) to obtain the title compound (34 mg, 0.10 mmol) having the following physical properties:

$^1$H NMR (400 MHz, CDCl$_3$): δ2.29 (3H, s), 2.49 (3H, s), 2.92 (2H, m), 3.50 (2H, m), 5.13 (1H, m), 5.62 (1H, br. d), 6.81 (1H, s), 6.91 (1H, dd, J=2 Hz, 8 Hz), 6.98 (1H, s), 7.24 (1H, d, J=8 Hz), 8.47 (1H, s).

MS (FAB): m/z 340 (M+H)$^+$.

Example 36

4-(5-benzoyloxyindan-2-yl)amino-5-methylthieno[2,3-d]pyrimidine a) 2-(tert-butoxycarbonylamino)-5-hydroxyindan (100 mg, 0.40 mmol) synthesized in Preparation Example 1 was dissolved in dry methylene chloride (2 ml), to which pyridine (0.15 ml, 1.8 mmol) and benzoyl chloride (0.14 ml, 1.1 mmol) were added, and the mixture was stirred overnight at room temperature. The reaction mixture was concentrated under reduced pressure, to which diethylether was added. The organic layer was washed with, in the order of, an aqueous solution of saturated potassium hydrogen sulfate, brine, an aqueous solution of saturated sodium hydrogen carbonate, and brine, and then was dried over anhydrous sodium sulfate. The residue obtained by distilling off the solvent under reduced pressure was purified by silica gel chromatography (hexane:ethyl acetate=3:1) to obtain 2-(tert-butoxycarbonylamino)-5-benzoyloxyindan (130 mg, 0.37 mmol) having the following physical properties:

$^1$H NMR (400 MHz, CDCl$_3$): δ1.45 (9H, s), 2.80 (2H, m), 3.29 (2H, m), 4.50 (1H, m), 4.78 (1H, m), 7.00 (1H, dd, J=2 Hz, 8 Hz), 7.07 (1H, s), 7.25 (1H, d, J=8 Hz), 7.51 (2H, t, J=8 Hz), 7.63 (1H, t, J=7 Hz), 8.20 (2H, d, J=7 Hz).

MS (FAB): m/z 354 (M+H)$^+$, 298 (M+H−56)$^+$.

b) Using 5-benzoyloxy-2-(tert-butoxycarbonylamino) indan (130 mg, 0.37 mmol), 4N hydrochloric acid-dioxane (2 ml) and acetic acid (6 ml), a similar procedure to Example 24 was carried out to obtain 5-benzoyloxy-2-aminoindan hydrochloride (67 mg, 0.35 mmol) having the following physical properties:

$^1$H NMR (400 MHz, DMSO-d$_6$): δ3.00 (2H, m), 3.31 (2H, m), 4.06 (1H, m), 7.11 (1H, dd, J=2 Hz, 8 Hz), 7.21 (1H, d, J=2 Hz), 7.36 (1H, d, J=8 Hz), 7.61 (2H, t, J=8 Hz), 7.56 (1H, t, J=7 Hz), 8.12 (2H, d, J=7 Hz), 8.20 (3H, br. s).

c) Using 5-benzoyloxy-2-aminoindan hydrochloride (67 mg, 0.35 mmol), 4-chloro-5-methylthieno[2,3-d]pyrimidine (68 mg, 0.37 mmol), triethylamine (0.52 ml, 3.7 mmol), and ethanol (6 ml), a similar procedure to b) in Example 19 was carried out. The product obtained was purified by silica gel chromatography (hexane:ethyl acetate=2:1) to obtain the title compound (70 mg, 0.17 mmol) having the following physical properties:

$^1$H NMR (400 MHz, CDCl$_3$): δ2.51 (3H, s), 2.96 (2H, m), 3.53.(2H, m), 5.17 (1H, m), 5.65 (1H, br. d), 6.82 (1H, s), 7.04 (1H, dd, J=2 Hz, 8 Hz), 7.13 (1H, s), 7.30 (1H, d, J=8 Hz), 7.51 (2H, t, J=8 Hz), 7.64 (1H, t, J=8 Hz), 8.20 (2H, d, J=8 Hz), 8.48 (1H, s).

MS (FAB): m/z 402 (M+B)$^+$.

Example 37

6-(2-indanylamino)purine

Using 6-chloropurine (150 mg, 1.0 mmol), 2-aminoindan (200 mg, 1.5 mmol), and ethanol (6 ml), a similar procedure to Example 1 was carried out. The precipitate obtained was crystallized from ethanol to obtain the title compound (100 mg, 0.40 mmol) having the following physical properties:

mp: 300° C. or higher $^1$H NMR (400 MHz, DMSO-d$_6$): δ3.03 (2H, m), 3.27 (2H, n), 5.00 (1H, m), 7.16 (2H, m), 7.23 (2H, m), 7.79 (1H, br. s), 8.09 (1H, br. s), 8.21 (1H, br. s), 13.0 (1H, br.).

MS (FAB): m/z 252 (M+H)$^+$.

Example 38

4-(2-indanylamino)thieno[3,2-d]pyrimidine a) 3-aminothiophene-2-carboxylic acid methylester (1.6 g, 10 mmol) was added to formamide (3.4 ml), and the mixture was stirred at 200° C. for 2 hours. The reaction mixture was returned to room temperature, and water was added thereto, which was extracted with chloroform. The solid obtained by distilling off the solvent under reduced pressure was washed with ethyl acetate to obtain 4-hydroxythieno[3,2-d]pyrimidine (60 mg, 0.39 mmol).

$^1$H NMR (400 MHz, DMSO-d$_6$): δ7.40 (1H, m), 8.14 (1H, s), 8.18 (1H, m), 12.47 (1H, broad).

b) Using 4-hydroxythieno[3,2-d]pyrimidine (60 mg, 0.39 mmol), and phosphorus oxychloride (0.6 ml), and then 2-aminoindan (210 mg, 1.56 mmol), a similar procedure to Example 5 was carried out. The product obtained was purified by silica gel chromatography (hexane:ethyl acetate=1:2) to obtain the title compound (30 mg, 0.11 mmol) having the following physical properties:

$^1$H NMR (400 MHz, DMSO-d$_6$): δ3.02 (2H, dd, J=6 Hz, 16 Hz), 3.32 (2H, m), 4.98 (1H, m), 7.16 (2H, m), 7.25 (2H, m), 7.37 (1H, d, J=5 Hz), 8.08 (1H, m), 8.09 (1H, d, J=5 Hz), 8.48 (1H, s).

MS (FAB); m/z 268 (M+B)$^+$.

Experiment 1. Effect of compounds on the expression of the human inducible NO synthase (hiNOS) gene The experiment was carried out using A5 cells (human lung carcinoma cell line A549 cells (ATCC, CCL185) stably transfected with NOS53+F) previously reported by the inventors (Nunokawa, Y. et al., (1997) Biochem. Biophys. Res. Commun. 233, 523–526).

Compounds described in Examples were added to A5 cells simultaneously with IL-1β (1 ng/ml)+TNF-α (500 ng/ml) to investigate the inhibitory effect on the firefly luciferase activity 24 hours later.

The activity of firefly luciferase was measured based on the protocol by the Luciferase Assay System (Promega, U.S.A.).

The inhibitory effect of the compounds claimed in the present invention on the expression of the hiNOS gene was expressed as IC$_{50}$ value in Table 1.

TABLE 1

| Compounds tested | IL-1β + TNF-α stimulation IC$_{50}$ (μM) |
| --- | --- |
| Example 1 | 0.28 |
| Example 6 | 0.80 |
| Example 22 | 0.064 |
| Example 25 | 0.15 |
| Example 31 | 0.0024 |
| Example 32 | 0.051 |

Experiment 2. Effect of compounds on A549 cells (A549/NF-κBLuc) stably transfected with luciferase plasmid (pNFκB-Luc) having the NF-κB regulatory sequence Using lipofectamine (Lifetech oriental K.K., Tokyo), pNFκB-Luc (Stratagene, U.S.A.) were cotransfected with pSV2neo (Clontech, U.S.A.) into A549 cells according to the conventional method, and A549/NF-κBLuc stably transfected with pNFκB-Luc were selected by adding G418 sulfate ((1 mg/ml) Lifetech Oriental K.K.) to the culture medium.

It was found that when A549/NF-κBLuc was stimulated with IL-1β (1 ng/ml) or TNF-α (500 ng/ml) for 4 hours, the compounds claimed in the present invention inhibit the activity of firefly luciferase that is under the control of the activation of NF-κB. NF-κB inhibiting activity was expressed as $IC_{50}$ values in Table 2.

However, A5 cells used in Experiment 1 transfected with the sea pansy luciferase gene (pRL-SV40, Promega, U.S.A.) that is under the control of SV40 promoter that is independent of the activation of NF-κB exhibit the luciferase activity of sea pansy in the absence of stimulation, while the exposure of the compounds of the present invention (compounds in Example 31 and 32) at 1 μg/ml for 4 hours had no influence on the activity of sea pansy luciferase. This revealed that the compounds of the present invention specifically inhibit the activation of NF-κB.

The activity of sea pansy luciferase was measured based on the protocol by the Dual Luciferase Reporter Assay System (Promega, U.S.A.).

TABLE 2

| Compounds tested | IL-1β stimulation $IC_{50}$ (μM) | TNF-α stimulation |
|---|---|---|
| Example 1 | 0.71 | 1.1 |
| Example 22 | 0.064 | 0.13 |
| Example 25 | 0.15 | not determined |
| Example 31 | 0.072 | 0.12 |
| Example 32 | 0.051 | 0.089 |

Experiment 3. Effect of lipopolysaccharide (LPS) stimulation on NO and TNF-α production When various cells are stimulated with LPS, NV-κB is activated which results in the expression and induction of proteins represented by NOS, TNF-α, and thereby the cells start to produce NO and/or TNF-α.

To determine the production of NO indirectly, the Griess' method utilizing a diazo reaction is useful (Green, L. C. et al., (1982) Anal. Biochem, 126, 131–138). In the Griess' method, the Griess' reagent prepared by mixing naphthyl-ethylenediamine and sulfanilic acid is reacted with $NO_2^-$ ion in the culture medium, and the color development thereof is measured by an absorbance at 540 nm.

By determining the accumulation of NO in the culture medium released from mouse macrophage RAW264.7 cells (ATCC, TIB-71) stimulated with LPS (10 μg/ml) at 24 hours after the stimulation by the present method, it was revealed that NO production could be inhibited by adding the compounds described in Examples in the culture medium.

The determination by Biotrak Mouse TNF-α ELISA kit (Amersham Lifescience, England) also revealed that compounds illustrated in Examples can inhibit even the production of TNF-α released from RAW264.7 cells that were stimulated with LPS for 4 hours.

The inhibitory effect of these compounds was expressed as $IC_{50}$ value in Table 3.

TABLE 3

| Compounds tested | NO production $IC_{50}$ (μM) | TNF-α production |
|---|---|---|
| Example 1 | 0.71 | 1.1 |
| Example 22 | 0.064 | 0.16 |
| Example 31 | 0.024 | 0.048 |
| Example 32 | 0.025 | 0.051 |

Experiment 4.

An aqueous solution of 1% λ-carrageenin (Wako Pure Chemical Industries) in physiological saline (0.1 ml) was intradermally administered to the pad of the left paw of 6-week old male Wistar rats weighing 149 g to 171 g, and changes in the volume of the paw were measured for indicated period. The test compound (0.3, 1 mg/kg) described in Example 32 was suspended in a solution of 0.5% hydroxypropyl cellulose in physiological saline (EPC, Nippon Soda Co., Ltd.) and was intraperitoneally given 15 minutes before the administration of carrageenin. For the control group, a solution of 0.5% HPC in physiological saline was used. The result, shown in the next Figure, revealed that the compound in Example 32 at a dose of 1 mg/kg significantly suppressed edema formation at 2 hours and also exhibited a high rate of edema suppression at 3 hours and after.

Industrial Applicability

Since the compounds of the present invention can inhibit the activation of NF-κB, they are useful as preventive and therapeutic agents for diseases caused by the activation of NF-κB, for example diseases caused by the excessive production of various inflammatory mediators and viral propagation. Specifically, the NF-κB inhibitors of the present invention are useful as therapeutic and preventive agents for diseases caused by, for example, the excessive production of NO or TNF-α including sepsis, osteoarthritis, rheumatoid arthritis, cachexia, multiple organ failure, inflammatory bowel diseases, malaria, acquired immune deficiency syndrome, human T-cell leukemia, meningitis, hepatitis, type II diabetes, multiple sclerosis, Behcet disease, systemic lupus erythematosus, ischemic heart diseases such as myocardial infarction, cerebral ischemic disease and neurodegenerative diseases such as Alzheimer's disease, and the like.

What is claimed is:

1. A compound represented by the following formula (I):

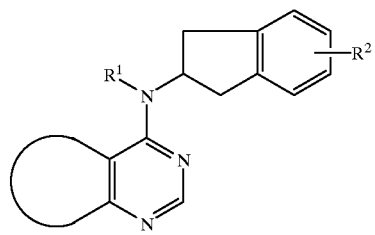

wherein
  $R^1$ represents a hydrogen atom or an alkyl group having 1 to 4 carbons, and
  $R^2$ represents a hydrogen atom,
    a —$OR^3$ group, wherein $R^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), a —OCOR$^4$ group, wherein R$^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), a —COOR$^5$ group, wherein R$^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), a —CONR$^6$R$^7$ group, wherein R$^6$ and R$^7$, which may be the same or different, each represent a hydrogen atom, an alkly group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), or R$^6$ and R$^7$, together with the nitrogen atom to which they are attached, represent a heterocyclic group that may further contain a nitrogen atom, an oxygen atom or a sulfur atom, or a —CH=CHR$^8$ group (in the group, R$^8$ represents an alkyl group having 1 to 4 carbons, or an optionally substituted phenyl group), and

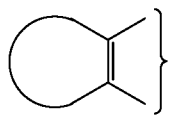

represents a skeleton selected from the group consisting of

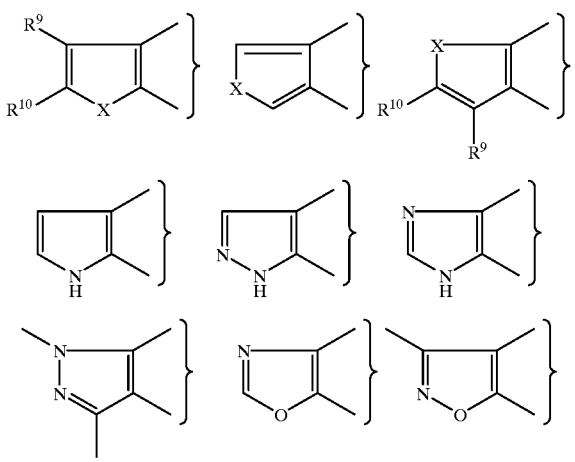

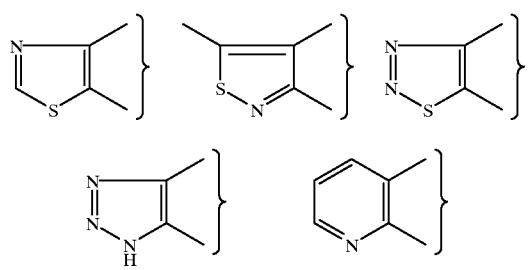

wherein R$^9$ and R$^{10}$, which may be the same or different, each represent a hydrogen atom, a halogen atom, a nitro group, a cyano group, a hydroxy group, an optionally substituted amino group, an optionally esterified or amidated carboxyl group, an alkyl group having 1 to 4 carbons, an alkyloxy group having 1 to 4 carbons, an optionally substituted phenyl group, an optionally substituted aralkyl group having 7 to 11 carbons, or an optionally substituted heterocyclic group, or R$^9$ and R$^{10}$ together form

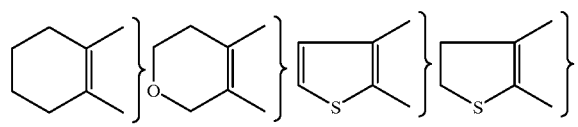

and X represents an oxygen atom or a sulfur atom; or a pharmaceutically acceptable salt thereof.

2. The compound according to claim 1 wherein R$^2$ represents a hydrogen atom, or a pharmaceutically acceptable salt thereof.

3. The compound according to claim 1 wherein R$^2$ represents a —OR$^3$ group, wherein R$^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), or a pharmaceutically acceptable salt thereof.

4. The compound according to claim 1 wherein R$^2$ represents a —OCOR$^4$ group, wherein R$^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), or a pharmaceutically acceptable salt thereof.

5. The compound according to claim 1 wherein R$^2$ represents a —COOR$^5$ group, wherein R$^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH2)n A group (n is 0, or an integer of 1, 2 or 3, and A is a heterocyclic group), or a pharmaceutically acceptable salt thereof.

6. The compound according to claim 1 wherein R$^2$ represents a —CONR$^6$R$^7$ group, wherein R$^6$ and R$^7$, which may be the same or different, each represent a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH²)n A group (n is 0, or an integer of 1, 2 or 3, and A is a heterocyclic group), or $R^6$ and $R^7$, together with the nitrogen atom to which they are attached, represent a heterocyclic group that may further contain a nitrogen atom, an oxygen atom or a sulfur atom, or a pharmaceutically acceptable salt thereof.

7. The compound according to claim 1 wherein $R^2$ represents a —CH=CHR$^8$ group (in the group $R^8$ represents an alkyl group having 1 to 4 carbons, or an optionally substituted phenyl group), or a pharmaceutically acceptable salt thereof.

8. Any one of the following compounds, or pharmaceutically acceptable salt thereof:

4-(2-indanylamino)-5-methylthieno(2,3-d)pyrimidine;
4-(2-indanylamino)thieno(3,4-d)pyrimidine;
4-(2-indanylamino)-7-methylthieno(3,2-d)pyrimidine;
4-(2-indanylamino)pyrrolo(2,3-d)pyrimidine;
4-(2-indanylamino)thieno(2,3d)pyrimidine;
4-(2-indanylamino)furo(2,3-d)pyrimidine;
4-(2-indanylamino)pyrazolo(3,4-d)pyrimidine;
7-(2-indanylamino)-v-triazolo(4,5-d)pyrimidine;
7-(2-indanylamino)oxazolo(5,4-d)pyrimidine;
3-methyl-4-)2-indanylamino)isoxazolo(5,4-d)pyrimidine;
7-(2-indanylamino)thiazolo(5,4-d)pyrimidine;
2-(2-indanylamino)-1-thia-2,3,5,7-tetraazaindene;
6-(2-indanylamino)-7-methylisothiazolo(3,4-d)pyrimidine;
7-(2-indanylamino)-1,3-dimethyl-1H-pyrazolo(4,3-d) pyrimidine;
4-(2-indanylamino)pyrido(2,3-d)pyrimidine;
4-(N-(2-indanyl)-N-methylamino)-5-methylthieno(2,3-d) pyrimidine;
4-(2-indanylamino)-5-phenylthieno(2,3-d)pyrimidine;
4-(2-indanylamino)-5-(2-thienyl)thieno(2,3-d)pyrimidine;
5-(2-furyl)-4-(2-indanylamino)thieno(2,3-d)pyrimidine;
4-(2-indanylamino)-5,6-dimethylthieno(2,3-d)pyrimidine;
4-(2-indanylamino)-5-(6-(3-methylpyridyl))thieno(2,3-d) pyrifnidine;
4-(2-indanylamino)-5-isopropylthieno(2,3-d)pyrimidine;
4-(5-methoxyindan-2-yl)amino-5-methylthieno(2,3-d) pyrimidine;
4-(5-hydroxyindan-2-yl)amino-5-methylthieno(2,3-d) pyrimidine;
4-(5-phenoxyindan-2-yl)amino-5-methylthieno(2,3-d) pyrimidine;
4-(5-((E)-2-(4-methylphenyl)ethenyl)indan-2-yl)amino-5-methylthieno(2,3-d)pyrimidine;
4-(5-methoxycarbonylindan-2-yl)amino-5-methylthieno(2,3-d)pyrimidine;
4-(5-carboxyindan-2-yl)amino5-methylthieno(2,3-d) pyrimidine sodium salt;
N-propyl-2-(5-methylthieno(2,3-d)pyrimidine-4-yl)amino-5-indancarboxamide;
N-phenyl-2-(5-methylthieno(2,3-d)pyrmidine-4-yl)amino-5-indancarboxamide;
N-benzyl-2-(5-methylthieno(2,3-d)pyrimidine-4-yl)amino-5-indancarboxamide;
2-(5-methylthieno(2,3-d]pyrimidine-4-yl)aminoindan-5-carboxylic acid morpholinamide;
4-(4-methoxyindan-2-yl)amino-5-methylthieno(2,3-d) pyrimidine;
4-(4-methoxycarbonylindan-2-yl)amino-5-methylthieno (2,3 -d)pyrimidine;
4-(5-acetoxyindan-2-yl)amino-5-methylthieno(2,3-d) pyrimidine;
4-(5-benzoyloxyindan-2-yl)amino-5-methylthieno(2,3-d) pyrimidine;
6-(2-indanylamino)purine; and
4-(2-indanylamino)thieno(3,2d)pyrimidine.

9. A composition for inhibiting NF-κB comprising as an active ingredient a compound according to claim 1 or a pharmaceutically acceptable salt thereof.

* * * * *